(12) United States Patent
Schwartz et al.

(10) Patent No.: US 8,486,947 B2
(45) Date of Patent: Jul. 16, 2013

(54) TREATMENT OF PARKINSON'S DISEASE, OBSTRUCTIVE SLEEP APNEA, DEMENTIA WITH LEWY BODIES, VASCULAR DEMENTIA WITH NON-IMIDAZOLE ALKYLAMINES HISTAMINE $H_3$-RECEPTOR LIGANDS

(75) Inventors: Jean-Charles Schwartz, Paris (FR); Jeanne-Marie Lecomte, Paris (FR)

(73) Assignee: Bioprojet, Paris (FR)

( * ) Notice: Subject to any disclaimer, the term of this patent is extended or adjusted under 35 U.S.C. 154(b) by 1096 days.

(21) Appl. No.: 11/909,778

(22) PCT Filed: Mar. 30, 2006

(86) PCT No.: PCT/IB2006/000739
§ 371 (c)(1),
(2), (4) Date: Sep. 26, 2007

(87) PCT Pub. No.: WO2006/103546
PCT Pub. Date: Oct. 5, 2006

(65) Prior Publication Data
US 2009/0318433 A1 Dec. 24, 2009

Related U.S. Application Data

(60) Provisional application No. 60/668,618, filed on Apr. 6, 2005.

(30) Foreign Application Priority Data

Apr. 1, 2005 (EP) ..................................... 05290727

(51) Int. Cl.
*A61K 31/496* (2006.01)
(52) U.S. Cl.
USPC ................................ 514/252.12; 514/252.14
(58) Field of Classification Search
USPC ...................................... 514/252.12, 252.14
See application file for complete search history.

(56) References Cited

U.S. PATENT DOCUMENTS

| | | | |
|---|---|---|---|
| 4,707,487 A | 11/1987 | Arrang et al. |
| 5,290,790 A | 3/1994 | Arrang et al. |
| 5,463,074 A | 10/1995 | Shih et al. |
| 5,559,113 A | 9/1996 | Schwartz et al. |
| 5,578,616 A | 11/1996 | Aslanian et al. |
| 5,639,775 A | 6/1997 | Durant et al. |
| 5,663,350 A | 9/1997 | Durant et al. |
| 5,990,317 A | 11/1999 | Phillips et al. |
| 6,080,871 A | 6/2000 | Kalindjian et al. |
| 6,166,060 A | 12/2000 | Phillips et al. |
| 6,248,765 B1 | 6/2001 | Schwartz et al. |
| 6,794,405 B2 | 9/2004 | Rong et al. |
| 6,797,726 B1 | 9/2004 | Ono et al. |
| 6,855,560 B1 | 2/2005 | Lovenberg et al. |
| 6,884,803 B2 | 4/2005 | Apodaca et al. |
| 7,138,413 B1 | 11/2006 | Schwartz et al. |
| 7,265,135 B2 | 9/2007 | Bogenstaetter et al. |
| 7,279,491 B2 | 10/2007 | Apodaca et al. |
| 7,547,693 B2 | 6/2009 | Ohtake et al. |
| 7,595,316 B2 | 9/2009 | Ohtake et al. |
| 8,106,041 B2 | 1/2012 | Schwartz et al. |
| 2002/0049277 A1 | 4/2002 | Yabe et al. |
| 2002/0065278 A1 | 5/2002 | Apodaca et al. |
| 2002/0137931 A1 | 9/2002 | Bennani et al. |
| 2004/0006120 A1 | 1/2004 | Yates et al. |
| 2005/0245587 A1 | 11/2005 | Brotchie et al. |

FOREIGN PATENT DOCUMENTS

| | | |
|---|---|---|
| EP | 680 960 | 11/1995 |
| EP | 0 982 300 | * 1/2000 |
| EP | 0 982 300 | 3/2000 |
| JP | 06345642 | 12/1994 |
| WO | WO-92/15567 | 9/1992 |
| WO | WO-93/12107 | 6/1993 |
| WO | WO-95/06037 | 3/1995 |
| WO | WO-95/11894 | 5/1995 |
| WO | WO-96/40126 | 12/1996 |
| WO | WO-2005/014579 | 2/2005 |

OTHER PUBLICATIONS

Vgontzas et al., Arch. Intern. Med., 1998;158:1333-1337.*
Dixon et al., Chest 2003;123:1134-1141.*
Chervin, Chest 2000;118:372-379.*
Alguacil L.F., et al "Histamine H3 receptor; a potential drug target for the treatment of central nervous system disorders.", Oct. 2003, pp. 303-313, vol. 2, No. 5, Current Drug Targets, CNS and Neurological Disorders.
Liedtke Susanna, et al, "Replacement of imidazole by a piperidine moiety differentially affects the potency of histamine H3-receptor antagonists", Jan. 2003, pp. 43-50, vol. 367, No. 1, Naunyn-Schmiedeberg's Archives of Pharmacology, Berlin, Germany.
Office Action mailed Jan. 17, 2012 in Japanese Application No. 2008-503613.
Office Action mailed Sep. 11, 2012 in Japanese Application No. 2008-503613.
Monti et al, "Effects of selective activation or blockade of the histamine H3 receptor on sleep and wakefulness", 1991, pp. 283-287, vol. 205, European Journal of Pharmacology.
Taneyoshi Nozawa, Treatment, 1999, vol. 8, No. 3, pp. 1141-1146.
Liedtke, S. et al., Naunyn-Schmiedeberg's archives of pharmacology, 2003, vol. 367, No. 1, pp. 43-50.
Manfredi, R.L. et al, Seminars in neurology, 1987, vol. 7, No. 3, pp. 250-258.
Current drug targets, CNZ and neurological disorders, 2003, vol. 2, No. 5, pp. 303-313.
Masayuki Miyamoto, et al., Geriatr Med., vol. 40, No. 9, pp. 1237-1243.

* cited by examiner

*Primary Examiner* — San-Ming Hui
(74) *Attorney, Agent, or Firm* — B. Aaron Schulman, Esq.; Stites & Harbison, PLLC

(57) ABSTRACT

The present invention provides new method of treatment of Parkinson's disease, obstructive sleep apnea, narcolepsy, dementia with Lewy bodies, vascular dementia with non-imidazole alkylamine derivatives that constitute antagonists of the $H_3$-receptors of histamine.

18 Claims, No Drawings

TREATMENT OF PARKINSON'S DISEASE, OBSTRUCTIVE SLEEP APNEA, DEMENTIA WITH LEWY BODIES, VASCULAR DEMENTIA WITH NON-IMIDAZOLE ALKYLAMINES HISTAMINE $H_3$-RECEPTOR LIGANDS

The present invention relates to the therapeutical application of alkylamines of formula (A) as defined hereafter for the treatment of Parkinson's disease (PD), obstructive sleep apnea (OSA), dementia with Lewy bodies (DLB) and/or vascular dementia (VD), and particularly for the treatment of their symptoms.

Antagonists of histamine $H_3$-receptor are known especially to increase synthesis and release of cerebral histamine. Through this mechanism, they induce an extended wakefulness, an improvement in cognitive processes, a reduction in food intake and a normalization of vestibular reflexes (Schwartz et al., Physiol. Rev., 1991, 71: 1-51).

Histamine $H_3$-receptor agonists are known to inhibit the release of several neurotransmitters including histamine, monoamines and neuropeptides and thereby exert sedative and sleep-promoting effects in brain. In peripheral tissues, $H_3$-receptor agonists exert namely anti-inflammatory, antinociceptive, gastrointestinal, antisecretory smooth muscle decontracting activities.

$H_3$ receptor antagonist or agonist compounds previously known resemble histamine in possessing an imidazole ring generally monosubstituted in 4(5)-position (Ganellin et al., Ars Pharmaceutica, 1995, 36:3, 455-468; Stark et al., Drug of the Future, 1996, 21(5), 507-520).

Numerous patents and patent applications are directed to antagonist and/or agonist compounds having such structure, in particular EP 197 840, EP 494 010, WO 93/14070, WO 96/29315, WO 92/15 567, WO 93/20061, WO 93/20062, WO 95/11894, U.S. Pat. No. 5,486,526, WO 93/12107, WO 93/12108, WO 95/14007, WO 95/06037, WO 97/29092, EP 680 960, WO 96/38141, WO 96/38142, WO 96/40126.

In the literature, Plazzi et al., Eur. J. Med. Chem. 1995, 30, 881, Clitherow et al., Bioorg. & Med. Chem. Lett. 6 (7), 833-838 (1996) Wolin et al., Bioorg. & Med. Chem., Lett; 8, 2157 (1998) can be cited also in this respect.

Nevertheless, such imidazole derivatives may show drawbacks such as poor blood-brain barrier penetration, interaction with cytochrome P-450 proteins and/or some hepatic and ocular toxicities.

Non-imidazole known neuro-active compounds such as betahistine (J-M. Arrang et al., Eur, J. Pharmacol. 1985, 111: 72-84), phencyclidine (J-M. Arrang et al., Eur. J. Pharmacol. 1988, 157: 31-35), dimaprit (J-C Schwartz et al., Agents Actions 1990, 30: 13-23), clozapine (M. Kathmann et al., Psychopharmacology 1994, 116: 464-468), and sesquiterpenes (M. Takigawa et al., JP 06 345 642 (20 Dec. 1994)) were suggested to display $H_3$-receptor antagonism but all these compounds have only very low potency.

These compounds were previously known as therapeutic agent before the discovery and characterization of the histamine $H_3$-receptor, in particular as neuro-active agents for example as neuroleptic (clozapine) or psychotomimetic (Phencyclidine) agent.

When tested at the $H_3$-receptor, these compounds were shown to display much lower potency than the imidazole-containing compounds described in patent applications quoted above.

Contrary to previous attempts, the inventors succeeded at developing potent $H_3$-receptor ligands not containing imidazole ring that reduced the above-mentioned drawbacks. These compounds, their preparation and therapeutical applications thereof have been described in the international patent application WO 00/06254.

The participation of histamine, particularly when acting through its H3 Receptor (H3R), in the etiology or symptomatology of PD, OSA, DLB or VD has never been reported before.

PD is mainly associated with a degeneration of dopaminergic neurons in the nigrostriatal tract from which derive the motor impairments and neuropsychiatric disorders characteristic of the disease. Whereas some other aminergic neuron classes might be affected in the parkinsonian brain, post-mortem neurochemical and immunohistochemical studies have shown that histaminergic neurons are completely spared from the degeneration process (Garbarg et al., Lancet 1983, 1, 74; Nakamura et al., Neurology, 1996, 4, 1693). In addition, in a model of "Parkinsonian" rat, in which the nigrostriatal dopaminergic neurons had been previously destroyed by unilateral administration of the neurotoxin 6-hydroxydopamine, the effect of the antiparkinsonian drug levodopa on the turning behaviour, a reflect of its antiparkinsonian activity, was not modified by co-administration of thioperamide, a prototypical H3R antagonist/inverse agonist (Huotary et al., Parkinsonism Relat Disord, 2000, 6, 159). This absence of effect is not attributable to either an absence of H3R sites in the nigrostriatal complex where, on the contrary, they abund (Pillot et al., Neuroscience 2002, 114, 176) or a disappearance of H3R sites as a result of the neuronal degeneration process, since the number of these sites is, on the contrary, elevated in the same animal model (Ryu et al., Neurosci. Letters, 1994, 178, 19). Taken together these findings suggested the lack of therapeutic interest of this class of drugs in the management of PD.

In addition to the major signs of PD in the movement initiation and control which constitute the core of the disease, it has become apparent during the last decades that a large proportion (as large as 74-81%) of PD patients display sleep and vigilance disorders (Garcia-Borreguero et al., Sleep Med. Rev., 2003, 7, 115). These include disorders of sleep initiation and maintenance, sleep fragmentation, parasomnias (including nocturnal hallucinations), sleep disordered breathing and excessive daytime sleepiness (including narcolepsy or "sleep attacks", i.e. inappropriate and unintended falls into sleep while in daytime activity). It is not entirely clear whether this group of disorders is purely related to the PD itself or whether there is also some participation of the treatment by direct or indirect dopaminergic agonists. The treatment of this class of disorders, which may all result from a loss of circadian rythmicity, is poorly efficient: for instance modafinil treatment of excessive daytime sleepiness was tried with limited success and the indication for this stimulant drug of essentially unknown mechanism of action has not been recognized by health authorities.

Dementia with Lewy bodies (DLB) results from the accumulation of such bodies in the cortex (whereas their accumulation in the nigro-striatal complex is observed in PD, a related degenerative disease). It is characterized by cognitive impairment, attentional disturbances, hallucinations, depression and sleep disorders.

Vascular dementia, the second most frequent cause of dementia after Alzheimer's disease, is characterized by acute loss of memory, orientation and executive functions and is often associated with demonstrable cerebrovascular lesions in patients suffering from hypertension, diabetes, hyperlipidemia, sleep apnea for several years.

The inventors have now unexpectedly demonstrated that antagonists/inverse agonists of the H3R can markedly improve some major symptoms of these diseases.

Alkylamine Histamine $H_3$-receptor Antagonists

Compounds, the structure of which does not contain an imidazole moiety, which are useful as histamine $H_3$-receptor ligands, are herein described.

These compounds have the following general formula (A):

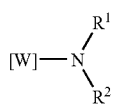
(A)

in which:
  W is a residue which imparts antagonistic and/or agonistic activity at histamine $H_3$-receptors when attached to an imidazole ring in 4(5)-position;
  $R^1$ and $R^2$ may be identical or different and represent each independently
    a lower alkyl or cycloalkyl,
or taken together with the nitrogen atom to which they are attached,
  a saturated nitrogen-containing ring

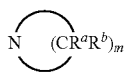
i)

with m ranging from 2 to 8, or
  a non-aromatic unsaturated nitrogen-containing ring

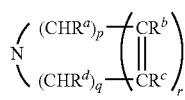
ii)

with p and q being from 0 to 3 independently and r being from 0 to 4, provided that p and q are not simultaneously 0 and $2 \leq p+q+r \leq 8$,
$R^{a-d}$ being independently a hydrogen atom or a lower alkyl, cycloalkyl, or carboalkoxy group, or
  a morpholino group, or
  a N-substituted piperazino group:

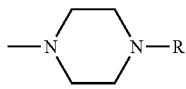

with R being a lower alkyl, cycloalkyl, carboalkoxy, aryl, arylalkyl, an alkanoyl or aroyl group.

Addition salts which the compounds form with pharmaceutically acceptable acids are also described. The pharmaceutically acceptable salts comprise the nontoxic salt of inorganic or organic acids. Examples of these salts include the hydrochloride, the hydrobromide or the hydrogen maleate or hydrogen oxalate.

The present application also describes the hydrates of the compounds, the hydrated salts of these compounds and the polymorphic crystalline structures.

When the compounds can exist in one or a number of isomeric forms according to the number of asymmetric centres in the molecule, the invention relates both to all the optical isomers and to their racemic modifications and the corresponding diastereoisomers. The separation of the diastereoisomers and/or of the optical isomers can be carried out according to methods known per se.

The present application also describes all the possible tautomeric forms of the compounds, whether these tautomers occur in isolated form or in the form of mixtures.

"Lower alkyl" or "cycloalkyl" is intended to mean a linear or branched alkyl group containing from 1 to 6 carbon atoms, or a saturated carbocycle containing 3 to 6 carbon atoms.

Typically examples of lower alkyl are methyl, ethyl, propyl, isopropyl and butyl groups.

A preferred group of compounds comprises those with $R^1$ and $R^2$ representing independently a lower alkyl group, especially an ethyl group.

Preferred compounds are also those of formula (A) in which $R^1$ and $R^2$ taken together with the nitrogen atom to which they are attached, form a saturated nitrogen-containing ring:

i)

especially with m being 4, 5 or 6, optionally substituted with an alkyl group ($R^a$), preferably a methyl group.

The groups $R^a$ and $R^b$ are identical or different for each ($CR^aR^b$) moiety.

Piperidyl and pyrrolidinyl moieties are especially preferred.

Another preferred group of compounds comprises compounds (A) in which $R^1$ and $R^2$ taken together with the nitrogen atom to which they are attached, form a non-aromatic unsaturated nitrogen-containing ring:

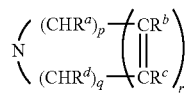
ii)

especially with p, q, and r being independently 1 or 2.

In this group, more preferred compounds are those with p being 2 and q and r each being 1.

A sub-class in this group comprises compounds with $R^{a-d}$ being each a hydrogen atom.

When $NR^1R^2$ is a nitrogen-containing ring i) or ii) as above-defined, the latter is preferably substituted with one or two lower alkyl group(s), especially a methyl group.

The position for substitution is preferably selected according the following order:
  meta>para>ortho.

In this group, for nitrogen-containing ring bearing only one substituent, this latter is preferably in meta position with respect to the nitrogen-atom.

For nitrogen-containing ring bearing two substituents, meta-meta substitution is preferred, especially when these two substituents are in trans-relation.

Piperidyl or pyrrolidinyl moiety substituted in meta or meta-meta position, especially with a methyl group, give particularly preferred compounds.

When $NR^1R^2$ represents a N-substituted piperazino group, R may be a lower alkyl e.g. methyl.

Typical examples of group R being an aryl or arylalkyl moiety are phenyl and benzyl.

R may be also an alkanoyl or aroyl group e.g. acetyl or benzoyl.

In all the possible groups for R, the alkyl moiety refers to a linear or branched chain containing from 1 to 6 carbon atoms.

The cycloalkyl group refers to a saturated carbocycle containing 3 to 7 carbon atoms.

When R represents an aryl or arylalkyl group, the aryl moiety is especially a phenyl group optionally substituted with one or more substituents selected from halogen atoms, advantageously selected from fluorine, chlorine and bromine, or a lower alkyl or cycloalkyl, a trifluoromethyl, aryl, alkoxy, aryloxy, nitro, formyl, alkanoyl, aroyl, arylalkanoyl, amino, carboxamido, cyano, alkyloximino, aryloximino, α-hydroxyalkyl, alkenyl, alkynyl, sulphamido, sulfamoyl, carboxamide, carboalkoxy, arylalkyl or oxime group.

R may be also an optionally substituted benzoyl, the substituent being as defined above with reference to the phenyl group.

Typical example of —$NR^1R^2$ representing a N-substituted piperazino group is N-acetylpiperazino.

According to one aspect, the compounds have the following general formula (I):

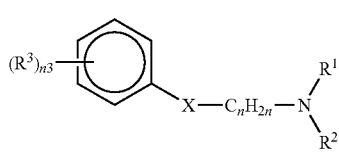

in which:
$C_nH_{2n}$ is a linear or branched hydrocarbon chain with n ranging from 2 to 8;
X is an oxygen or sulfur atom;
$n_3$ is an integer from 0 to 5;
$R^3$ represents each independently
  a halogen atom,
  a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, α-hydroxyalkyl, alkenyl, alkynyl, sulphamido, sulfamoyl, sulphonamido, carboxamide, carbonylcycloalkyl, alkylcarbonylalkyl, carboalkoxy, arylalkyl or oxime group,
  or taken together with the carbon atoms of the phenyl ring to which it is fused, a 5- or 6-membered saturated or unsaturated ring or a benzene ring.

$R^1$ and $R^2$ are as above-defined in formula (A).

A preferred group of compounds is the group composed of compounds of formula (I) in which X is an oxygen atom.

Another preferred group of compounds comprises compounds (I) in which —$C_nH_{2n}$— is a linear chain —$(CH_2)_n$— with n being as previously defined.

Preferred compounds are also those with n varying from 3 to 5, and with n being more preferably 3.

A sub-class of compounds according to the invention comprises the compounds of formula (I) with $n_3$ being zero that is those having an unsubstituted phenyl moiety.

Another group of compounds is composed of compounds containing one or more substituents $R^3$ which may be identical or different. In this group, the compounds having a mono- or di-substituted ($n_3$=1 or 2) phenyl moiety are preferred and those mono-substituted with one group $R^3$ as defined above in para-position are particularly preferred.

Among these compounds, (n3 being 1) $R^3$ is preferably a halogen atom or a cyano, nitro, alkanoyl, alkyloximino or α-hydroxyalkyl group.

Still more preferred compounds are those with $R^3$ being CN, $NO_2$, $COCH_3$, $COC_2H_5$, $H_3C-C=N-OH$, $H_3C-CH-OH$ and cycloalkyl-CO like cyclopropyl-CO.

$R^3$ being a halogen atom may be advantageously selected from fluorine, chlorine and bromine.

$R^3$ being an aryl group, may be especially a phenyl group.

In the other substituents $R^3$, the aryl moiety is advantageously a phenyl moiety.

$R^3$ being an aryloxy group may be especially a phenoxy group.

According to the invention, alkanoyl is intended to mean a group containing an alkyl moiety as defined above.

Typical examples of $R^3$ being an alkanoyl, aroyl or arylalkanoyl group are acetyl, butyryl and propionyl groups, benzoyl group or phenylacetyl group.

Typical examples of $R^3$ forming together with the carbon atoms of the phenyl ring to which it is fused, a saturated ring leads to 5,6,7,8-tetrahydronaphthyl or forming a benzene ring leads to a naphthyl moiety.

According to the invention, alkenyl or alkynyl group may contain advantageously from 1 to 8 carbon atoms, in particular from 1 to 6 carbon atoms and preferably 1 to 4 carbon atoms.

In carboalkoxy, carboxyamido, carbonylcycloalkyl, alkylcarbonylalkyl, or carboxamide groups, the hydrocarbon chain is saturated, linear or branched and contains an alkyl moiety as defined above.

In alkoxy, alkylalkoximino, alkyloximino, a-alkyloxyalkyl, arylalkyl or Y-hydroxyalkyl group, the alkyl moiety is as previously defined also.

Particularly preferred compounds are:
1-(5-phenoxypentyl)-piperidine
1-(5-phenoxypentyl)-pyrrolidine
N-methyl-N-(5-phenoxypentyl)-ethylamine
1-(5-phenoxypentyl)-morpholine
N-(5-phenoxypentyl)-hexamethyleneimine
N-ethyl-N-(5-phenoxypentyl)-propylamine
1-(5-phenoxypentyl)-2-methyl-piperidine
1-(5-phenoxypentyl)-4-propyl-piperidine
1-(5-phenoxypentyl)-4-methyl-piperidine
1-(5-phenoxypentyl)-3-methyl-piperidine
1-acetyl-4-(5-phenoxypentyl)-piperazine
1-(5-phenoxypentyl)-3,5-trans-dimethyl-piperidine
1-(5-phenoxypentyl)-3,5-cis-dimethyl-piperidine
1-(5-phenoxypentyl)-2,6-cis-dimethyl-piperidine
4-carboethoxy-1-(5-phenoxypentyl)-piperidine
3-carboethoxy-1-(5-phenoxypentyl)-piperidine
1-[3-(4-cyclopropylcarbonylphenoxy)propyl]-piperidine
1-[3-(4-acetylphenoxy)-2-R-methylpropyl]piperidine
1-[3-(4-cyanophenoxy)propyl]-4-methylpiperidine
1-[3-(4-cyanophenoxy)propyl]-3-methylpiperidine
1-[3-(4-acetylphenoxy)-2-S-methylpropyl]piperidine
1-{3-[4-(3-oxobutyl)phenoxy]propyl}piperidine
1-[3-(4-cyano-3-fluorophenoxy)propyl]piperidine
1-[3-(4-nitrophenoxy)propyl]-3-methylpiperidine
1-[3-(4-cyanophenoxy)propyl]-2-methylpiperidine
1-[3-(4-nitrophenoxy)propyl]-2-methylpiperidine
1-[3-(4-nitrophenoxy)propyl]-4-methylpiperidine
1-[3-(4-cyanophenoxy)propyl]-2,6-dimethylpiperidine
1-[3-(4-propionylphenoxy)propyl]-3-methylpiperidine 1-[3-(4-cyclobutylcarbonylphenoxy)propyl]piperidine
1-[3-(4-cyclopentylcarbonylphenoxy)propyl]piperidine
1-[3-(4-cyanophenoxy)propyl]-cis-2-methyl-5-ethylpiperidine
1-[3-(4-cyanophenoxy)propyl]-trans-2-methyl-5-ethylpiperidine
1-[3-(4-cyanophenoxy)propyl]-cis-3,5-dimethylpiperidine
1-[3-(4-propionylphenoxy)propyl]-4-methylpiperidine
1-[3-(4-propionylphenoxy)propyl]-2-methylpiperidine
1-{3-[4-(1-hydroxypropyl)phenoxy]propyl}-3-methylpiperidine
1-{3-[4-(1-hydroxypropyl)phenoxy]propyl}-4-methylpiperidine
1-[3-(4-propionylphenoxy)propyl]-2-methylpiperidine
1-[3-(4-propionylphenoxy)propyl]-4-methylpiperidine methoxime
1-[3-(4-cyanophenoxy)propyl]-trans-3,5-dimethylpiperidine
1-[3-(4-cyclopropyl carbonyl phenoxy)propyl]-trans-3,5-dimethylpiperidine
1-[3-(4-cyclopropyl carbonyl phenoxy)propyl]-cis-3,5-dimethylpiperidine
1-[3-(4-carbomethoxyphenoxy)propyl]piperidine
1-[3-(4-propenylphenoxy)propyl]-2-methyl piperidine
1-[3-(4-propionylphenoxy)propyl]-2-methylpiperidine
1-{3-[4-(1-ethoxypropyl)phenoxy]propyl}-2-methyl piperidine
1-[3-(4-propionylphenoxy)propyl]-4-methylpiperidine
1-[3-(4-bromophenoxy)propyl]piperidine
1-[3-(4-nitrophenoxy)propyl]piperidine
1-[3-(4-N,N-dimethylsulfonamidophenoxy)propyl]piperidine
1-[3-(4-isopropylphenoxy)propyl]piperidine
1-[3-(4-sec-butylphenoxy)propyl]piperidine
1-[3-(4-propylphenoxy)propyl]piperidine
1-[3-(4-ethylphenoxy)propyl]piperidine
1-(5-phenoxypentyl)-1,2,3,6-tetrahydropyridine
1-[5-(4-nitrophenoxy)-pentyl]-pyrrolidine
1-[5-(4-chlorophenoxy)-pentyl]-pyrrolidine
1-[5-(4-methoxyphenoxy)-pentyl]-pyrrolidine
1-[5-(4-methylphenoxy)-pentyl]-pyrrolidine
1-[5-(4-cyanophenoxy)-pentyl]-pyrrolidine
1-[5-(2-naphthyloxy)-pentyl]-pyrrolidine
1-[5-(1-naphthyloxy)-pentyl]-pyrrolidine
1-[5-(3-chlorophenoxy)-pentyl]-pyrrolidine
1-[5-(4-phenylphenoxy)-pentyl]-pyrrolidine
1-{5-[2-(5,6,7,8-tetrahydronaphthyl)-oxy]-pentyl}-pyrrolidine
1-[5-(3-phenylphenoxy)-pentyl]-pyrrolidine
1-(5-phenoxypentyl)-2,5-dihydropyrrole
1-{5-[1-(5,6,7,8-tetrahydronaphthyl)-oxy]-pentyl}-pyrrolidine
1-(4-phenoxybutyl)-pyrrolidine
1-(6-phenoxyhexyl)-pyrrolidine
1-(5-phenylthiopentyl)-pyrrolidine
1-(4-phenylthiobutyl)-pyrrolidine
1-(3-phenoxypropyl)-pyrrolidine
1-[5-(3-nitrophenoxy)-pentyl]-pyrrolidine
1-[5-(4-fluorophenoxy)-pentyl]-pyrrolidine
1-[5-(4-nitrophenoxy)-pentyl]-3-methyl-piperidine
1-[5-(4-acetylphenoxy)-pentyl]-pyrrolidine
1-[5-(4-aminophenoxy)-pentyl]-pyrrolidine
1-[5-(3-cyanophenoxy)-pentyl]-pyrrolidine
N-[3-(4-nitrophenoxy)-propyl]-diethylamine
N-[3-(4-cyanophenoxy)-propyl]-diethylamine
1-[5-(4-benzoylphenoxy)-pentyl]-pyrrolidine
1-{5-[4-(phenylacetyl)-phenoxy]-pentyl}-pyrrolidine
N-[3-(4-acetylphenoxy)-propyl]-diethylamine
1-[5-(4-acetamidophenoxy)-pentyl]-pyrrolidine
1-[5-(4-phenoxyphenoxy)-pentyl]-pyrrolidine
1-[5-(4-N-benzamidophenoxy)-pentyl]-pyrrolidine
1-{5-[4-(1-hydroxyethyl)-phenoxy]-pentyl}-pyrrolidine
1-[5-(4-cyanophenoxy)-pentyl]-diethylamine
1-[5-(4-cyanophenoxy)-pentyl]-piperidine
N-[5-(4-cyanophenoxy)-pentyl]-dimethylamine
N-[2-(4-cyanophenoxy)-ethyl]-diethylamine
N-[3-(4-cyanophenoxy)-propyl]-dimethylamine
N-[4-(4-cyanophenoxy)-butyl]-diethylamine
N-[5-(4-cyanophenoxy)-pentyl]-dipropylamine
1-[3-(4-cyanophenoxy)-propyl]-pyrrolidine
1-[3-(4-cyanophenoxy)-propyl]-piperidine
N-[3-(4-cyanophenoxy)-propyl]-hexamethyleneimine
N-[6-(4-cyanophenoxy)-hexyl]-diethylamine
N-[3-(4-cyanophenoxy)-propyl]-dipropylamine
N-3-[4-(1-hydroxyethyl)-phenoxy]-propyl-diethylamine
4-(3-diethylaminopropoxy)-acetophenone-oxime
1-[3-(4-acetylphenoxy)-propyl]-piperidine
1-[3-(4-acetylphenoxy)-propyl]-3-methyl-piperidine
1-[3-(4-acetylphenoxy)-propyl]-3,5-trans-dimethyl-piperidine
1-[3-(4-acetylphenoxy)-propyl]-4-methyl-piperidine
1-[3-(4-propionylphenoxy)-propyl]-piperidine
1-[3-(4-acetylphenoxy)-propyl]-3,5-cis-dimethyl-piperidine
1-[3-(4-formylphenoxy)-propyl]-piperidine
1-[3-(4-isobutyrylphenoxy)-propyl]-piperidine
N-[3-(4-propionylphenoxy)-propyl]-diethylamine
1-[3-(4-butyrylphenoxy)-propyl]-piperidine
1-[3-(4-acetylphenoxy)-propyl]-1,2,3,6-tetrahydropyridine
More preferred compounds are:
1-[5-(4-nitrophenoxy)-pentyl]-pyrrolidine
N-[3-(4-cyanophenoxy)-propyl]-diethylamine
N-[3-(4-acetylphenoxy)-propyl]-diethylamine
1-{5-[4-(1-hydroxyethyl)-phenoxy]-pentyl}-pyrrolidine
N-[4-(4-cyanophenoxy)-butyl]-diethylamine
1-[3-(4-cyanophenoxy)-propyl]-piperidine
N-[3-(4-cyanophenoxy)-propyl]-hexamethyleneimine
N-3-[4-(1-hydroxyethyl)-phenoxy]-propyl-diethylamine
4-(3-diethylaminopropoxy)-acetophenone-oxime
1-[3-(4-acetylphenoxy)-propyl]-3-methyl-piperidine
1-[3-(4-acetylphenoxy)-propyl]-4-methyl-piperidine
1-[3-(4-propionylphenoxy)-propyl]-piperidine Compounds of formula (I) in which:
—$NR^1R^2$ is a pyrrolidinyl group, $C_nH_{2n}$ is a linear chain —$(CH_2)_n$— and $n_3$ is zero, X being an oxygen atom with n ranging from 3 to 5, or X being a sulfur atom with n being 4 or 5;
—$NR^1R^2$ is a piperidinyl group, $C_nH_{2n}$ is a linear chain —$(CH_2)_n$— and X is an oxygen atom, $n_3$ being zero with n being 2, 5 or 8 or $n_3$ being 1 with $R^3$ being 4-CN and n being 5;
—$NR^1R^2$ is a diethylamine group, X is an oxygen atom, $C_nH_{2n}$ is a linear chain —$(CH_2)_n$— and $n_3$ is 1, $R^3$ being 4-$NO_2$ or 4-$COCH_3$ with n being 3 or $R^3$ being 4-CN with n being 2 to 4;
—$NR^1R^2$ is a dimethylamine group, X is an oxygen atom, $C_nH_{2n}$ is a linear chain —$(CH_2)_n$— and $n^3$ is 1, $R^3$ being 4-CN with n being 3,
are known in the art.

According to a second aspect, it is herein described non-imidazole compounds analogous to the compounds disclosed in WO 96/29315 and WO 93/14070.

Thus, a first sub-class of the compounds (A) is defined by the compounds having the following general formula (IIa) and (IIb):

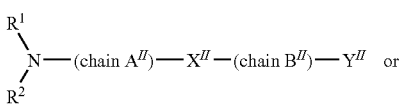
(IIa)

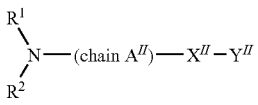
(IIb)

in which
R¹ and R² are as defined with reference to general formula (A);
the chain $A''$ represents a saturated or unsaturated, straight or branched hydrocarbon chain containing 1 to 6 carbon atoms, it being possible for the saturated hydrocarbon chain to be interrupted by a hetero atom such as a sulphur atom;
$X''$ represents an oxygen or sulphur atom, —NH—, —NHCO—, —N(alkyl)CO—, —NHCONH—, —NH—CS—NH—, —NHCS—, —O—CO—, —CO—O—, —OCONH—, —OCON(alkyl)-, —OCON(alkene), —OCONH—CO—, —CONH—, —CON(alkyl)-, —SO—, —CO—, —CHOH—, —N (saturated or unsaturated alkyl), —S—C(=NY")—NH—Y"— with the Y" identical or different and as defined previously, or —NR$_{II}$—C(=NR"$_{II}$)—NR'$_{II}$—, R$_{II}$ and R'$_{II}$ denoting a hydrogen atom or a lower alkyl radical and R"$_{II}$ a hydrogen atom or another powerful electronegative group, such as a cyano or COY$_1^{II}$ group, Y$_1^{II}$ denoting an alkoxy group;
the chain $B''$ represents an aryl, arylalkyl or arylalkanoyl group, a straight alkylene chain —$(CH_2)_{nII}$—, n being an integer which can vary between 1 and 5 or a branched alkylene chain containing from 2 to 8 carbon atoms, the alkylene chain being optionally interrupted by one or a number of oxygen or sulphur atoms, or a group —$(CH_2)_{nII}$—O— or —$(CH_2)_{nII}$—S— where n$_{II}$ is an integer equal to 1 or 2;
$Y''$ represents a straight or branched alkyl group containing 1 to 8 carbon atoms; a cycloalkyl containing 3 to 6 carbon atoms; a bicycloalkyl group; a cycloalkenyl group; an aryl group such as an optionally substituted phenyl group; a 5- or 6-membered heterocyclic radical containing one or two heteroatoms chosen from nitrogen and sulphur atoms, the said heterocyclic radical optionally being substituted; or also a bicyclic radical resulting from the fusion of a benzene ring to a heterocycle as defined above.

The chain A can be a straight alkylene chain —$(CH_2)_{nII}$—, n$_{II}$ representing an integer between 1 and 6 carbon atoms, preferably between 1 and 4 carbon atoms, or a branched alkylene chain, preferably a chain substituted by one or a number of methyl or ethyl radicals.

The chain $A''$ can also be a straight or branched unsaturated alkylene chain, and can be, for example, the allyl group.

When $Y''$ represents a cycloalkyl group, the latter can be, for example, cyclopentyl, cyclohexyl or a bicycloalkyl group.

When $Y''$ represents a substituted phenyl group, the phenyl group can be mono- or polysubstituted, for example, by a halogen, by a lower alkyl, for example $CH_3$, by $CF_3$, CN, $COCH_3$, COOR"$_1$, or OR"$_1$, R"$_1$, representing a lower alkyl, for example $COOCH_3$, the $NO_2$ group or the group NR"$_2$R"$_{13}$, R"$_{12}$ and R"$_3$ representing a hydrogen atom and/or a lower alkyl radical ("lower alkyl" means an alkyl radical containing at most 6 carbon atoms).

When $Y''$ represents a heterocyclic radical, the latter can be, for example, the pyridyl radical, the pyridyl N-oxide radical or the pyrazinyl radical, optionally mono- or polysubstituted by $NO_2$, $CF_3$, $CH_3$, $NH_2$, a halogen such as Cl, the $COOCH_3$ group or also the thiazolyl radical.

When $Y''$ represents a polycyclic radical resulting from condensed aromatic or heteroaromatic moieties the radical can be, for example, the benzothiazolyl, quinolinyl, isoquinolinyl radical or related moieties.

A second sub-class of the compounds (A) comprises the compounds having the above-formulae (IIa) and (IIb) in which:
R¹R² are as defined with reference to general formula (A);
the chain A" represents an unbranched, branched or unsaturated alkyl group —$(CH_2)_{nII}$— where n$_{II}$ is an integer which can vary between 1 and 8 and preferably between 1 and 4; an unbranched or branched alkene group comprising from 1 to 8 carbon atoms and preferably 1 to 4 carbon atoms; an unbranched or branched alkyne group comprising from 1 to 4 carbon atoms;
the group $X''$ represents —OCONH—; —OCON(alkyl)-; —OCON(alkene)-; —OCO—; —OCSNH—; —$CH_2$—; —O—; —$OCH_2$CO—; —S—; —CO—; —CS—; amine; saturated or unsaturated alkyl;
the chain $B''$ represents an unbranched, branched or unsaturated lower alkyl comprising from 1 to 8 carbon atoms and preferably 1 to 5 carbon atoms; —$(CH_2)_{nII}$ (hetero atom)—where the hetero atom is preferably a sulphur or oxygen atom; n$_{II}$ being an integer which can vary between 1 and 5, preferably between 1 and 4;
the group $Y''$ represents a phenyl group, unsubstituted or mono- or polysubstituted with one or more identical or different substituents selected from halogen atoms, $OCF_3$, CHO, $CF_3$, $SO_2N(alkyl)_2$ such as $SO_2N(CH_3)_2$, $NO_2$, S(alkyl), S(aryl), $SCH_2$(phenyl), an unbranched or branched alkene, an unbranched or branched alkyne optionally substituted with a trialkylsilyl radical, —O(alkyl), —O(aryl), —$CH_2$CN, a ketone, an aldehyde, a sulphone, an acetal, an alcohol, a lower alkyl, —CH=CH—CHO, —C(alkyl)=N—OH, —C(alkyl)=N—O(alkyl) and other keto derivatives, —CH=NOH, —CH=NO(alkyl), and other aldehyde derivatives, —C(alkyl)=NH—NH—CONH$_2$, an O-phenyl or —$OCH_2$(phenyl) group, —C(cycloalkyl)=NOH, —C(cycloalkyl)=N—O(alkyl), an optionally substituted heterocycle; a heterocycle comprising a sulphur hetero atom; a cycloalkyl; a bicyclic group and preferably a norbornyl group; a phenyl ring fused to a heterocycle comprising a nitrogen hetero atom or to a carbocycle or a heterocycle bearing a keto function; an unbranched or branched lower alkyl comprising from 1 to 8 carbon atoms; an unbranched or branched alkyne comprising from 1 to 8 carbon atoms and preferably 1 to 5 carbon atoms; a linear or branched alkyl mono- or polysubstituted with phenyl groups which are either unsubstituted or mono- or polysubstituted; a phenyl alkyl ketone in which the alkyl group is branched or unbranched or cyclic; a substituted or unsubstituted benzophenone; a substituted or unsubstituted, unbranched or branched or cyclic phenyl alcohol; an unbranched or branched alkene; a piperidyl group; a phenylcycloalkyl group; a polycyclic group, in particular a fluorenyl group, a naphthyl or polyhydronaphthyl group or an indanyl group; a phenol group; a ketone or keto derivative; a diphenyl group; a phenoxyphenyl group; a benzyloxyphenyl group.

Group $X^{II}$ representing an amine is understood to mean a secondary or tertiary amine.

The alkyl, alkene, alkyne, keto, aldehyde, cycloalkyl, S-alkyl, O-alkyl, phenyl alcohol and phenyl-cycloalkyl groups mentioned above as well as in the remainder of the description and the claims of the present patent comprise from 1 to 8 carbon atoms, and preferably 1 to 5.

Likewise, keto derivatives are understood to mean any oxime, alkyloxime, hydrazone, acetal, aminal, ketal, thione, carbazone or semicarbazone group and the thio analogues of these derivatives.

Likewise, by mono- or polysubstituted phenyl and/or benzophenone groups, it is understood to mean that these groups are substituted with one or more identical or different substituents selected from halogen atoms, $OCF_3$, CHO, $CF_3$, $SO_2N(alkyl)_2$, $SO_2N(CH_3)_2$, $NO_2$, S(alkyl), S(aryl), $SCH_2$(phenyl), an unbranched or branched alkene, an unbranched or branched alkyne optionally substituted with a trialkylsilyl radical, —O(alkyl), —O(aryl), —$CH_2CN$, a ketone, an aldehyde, a sulphone, an acetal, an alcohol, a lower alkyl, —CH=CH—CHO, —C(alkyl)=N—OH, —C(alkyl)=N—O(alkyl) an other keto derivatives, —CH=NOH, —CH=NO(alkyl), and other aldehyde derivatives, —C(alkyl)=NH—NH—$CONH_2$, an O-phenyl or —$OCH_2$(phenyl) group, —C(cycloalkyl)=NOH, —C(cycloalkyl)=N—O(alkyl), an optionally substituted heterocycle.

The keto substituent is preferably selected from a linear- or branched-chain aliphatic ketone, it being possible for the said chain to comprise from 1 to 8 carbon atoms and optionally to bear a hydroxyl group, a cycloalkyl ketone, an aryl alkyl ketone or aryl alkenyl ketone in which the aryl group is unsubstituted or mono- or polysubstituted, or a heteroaryl ketone in which the heteroaryl unit is preferably monocyclic.

The acetal substituent preferably consists of an aliphatic acetal comprising from 1 to 8 carbon atoms and optionally bearing a hydroxyl radical.

Group $Y^{II}$ representing a ketone is understood to mean, in particular, a ketone substituted with an alkyl or aryl group, it being possible for these groups to be substituted or unsubstituted.

As regards the heterocycles, these comprise from 1 to 3 hetero atoms, preferably sulphur, oxygen or nitrogen atoms.

The heterocycle substituent is preferably selected from an oxadiazole or an imidazole.

Preferred compounds (IIa) and (IIb) are those in which $X^{II}$ is selected from —O—, —NH—, —$CH_2$—, —OCONH—, —NHCO—, —NHCONH—. $X^{II}$ represents more preferably an oxygen atom.

Preferred compounds (IIa) and (IIb) are also those in which $Y^{II}$ is selected from a linear or branched alkyl group as above defined; a cycloalkyl group as above-defined, in particular cyclopentyl or cyclohexyl group; a phenyl group unsubstituted or mono-substituted, preferred substituent being halogen atom, in particular chorine; a heterocyclic radical, in particular pyridyl N-oxide or pyrazinyl radicals; a bicyclic radical such as a benzothiazolyl radical, $Y^{II}$ is preferably a phenyl group at least mono-substituted with —CHO, a ketone, an aldehyde, —CH=CH—CHO, —C(alkyl)=N—OH, —C(alkyl)=N—O(alkyl) and other keto derivatives, —CH=N—OH, —CH=NO(alkyl) and other aldehyde derivatives, —C(cycloalkyl)=NOH, —C(cycloalkyl)=N—O(alkyl).

$Y^{II}$ represents especially a phenyl group at least mono-substituted with a keto-substituent or an oxime-substituent, or an halogen atom.

Particularly preferred keto-substituent is cycloalkylketone.

Other preferred compounds are those wherein $Y^{II}$ represents a phenyl group fused to a carbocycle bearing a keto-function.

Yet other preferred $Y^{II}$ are phenylalkyl ketone in which the alkyl group is branched or unbranched or cyclic; an optionally substituted benzophenone, a ketone.

Particularly preferred group $Y^{II}$ are a phenyl group unsubstituted or mono-substituted as above-defined.

The chain $A^{II}$ is preferably a chain —$(CH_2)_{n_{II}}$— with $n_{II}$ varying from 1 to 6, preferably from 1 to 4. The chain $A^{II}$ represents especially —$(CH_2)_3$—.

Preferred chain $B^{II}$ is —$(CH_2)_2$— or —$(CH_2)_3$—.

Among compounds (IIa) and (IIb), particularly preferred compounds are those in which $X^{II}$ is an oxygen atom, the chain $A^{II}$ represents —$(CH_2)_3$— and, for compounds of formula (IIa), the chain $B^{II}$ represents —$(CH_2)_3$— also.

In this group, $Y^{II}$ is preferably an aryl group.

Preferred group $R^1$ and $R^2$ are as above-defined with reference to formula (A).

Examples of compounds (IIa) and (IIb) are:
3,3-Dimethylbutyl 3-piperidinopropyl ether
3-Phenylpropyl 3-piperidinopropyl ether
3-(4-Chlorophenyl)propyl 3-piperidinopropyl ether
2-Benzothiazolyl 3-piperidinopropyl ether
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chloro phenyl)propyl 3-(3,5-cis-dimethyl piperidino)propyl ether
3-(4-Chloro phenyl)propyl 3-(3,5-trans-dimethyl piperidino) propyl ether
3-Phenylpropyl 3-(N,N-diethylamino)propyl ether
N-Phenyl-3-piperidinopropyl carbamate
N-Pentyl-3-piperidinopropyl carbamate
(S)-(+)-N-[2-(3,3-Dimethyl)butyl]-3-piperidinopropyl carbamate
3-Cyclopentyl-N-(3-(1-pyrrolidinyl)propyl)propanamide
N-Cyclohexyl-N'-(1-pyrrolidinyl-3-propyl)urea
2-((2-Piperidinoethyl)amino)benzothiazole
5-Piperidinopentylamine
2-Nitro-5-(6-piperidinohexyl)pyridine
3-Nitro-2-(6-piperidinohexylamino)pyridine
2-(6-Piperidinohexylamino)pyrimidine
N-(6-Phenylhexyl)piperidine
N-(3-(N,N-Diethylamino)propyl)N'-phenylurea
N-Cyclohexylmethyl-N'-(3-piperidinopropyl)guanidine Preferred compounds according to the application of the invention include compounds of formula (IIa):

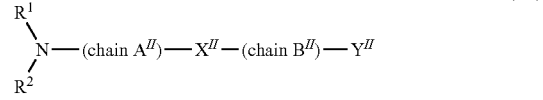

(IIa)

wherein:
$R^1$ and $R^2$ form together with the nitrogen atom to which they are attached a saturated nitrogen-containing ring

with m ranging from 2 to 8,
$R^{a-b}$ being independently a hydrogen atom or an alkyl containing 1 to 6 carbon atoms,
the chain $A^{II}$ selected from an unbranched alkyl group —$(CH_2)_{n_{II}}$— where $n_{II}$ is 3 the group $X^{II}$ is —O—;
the chain $B^{II}$ is an unbranched alkyl comprising 3 carbon atoms; and
the group $Y^{II}$ represents a phenyl group, unsubstituted or mono- or polysubstituted with one or more identical or different substituents selected from halogen atoms, $OCF_3$, CHO, $CF_3$, $SO_2N(alkyl)_2$ such as $SO_2N(CH_3)_2$, $NO_2$, S(aryl), $SCH_2$(phenyl), an unbranched or branched alkene or alkyne optionally substituted with a trialkylsilyl radical, —O(alkyl), —O(aryl), —$CH_2CN$, a ketone, an aldehyde, a sulphone, an acetal, an alcohol, a linear or branched alkyl group containing 1 to 6 carbon atoms, —CH=CH—CHO, —C(alkyl)=N—OH, —C(alkyl)=N—O(alkyl), —CH=NOH, —CH=NO(alkyl), —C(alkyl)=NH—NH—$CONH_2$, an O-phenyl or —$OCH_2$(phenyl) group, —C(cycloalkyl)=NOH, —C(cycloalkyl)=N—O(alkyl);
or their pharmaceutically acceptable salts, hydrates, or hydrated salts, or the polymorphic crystalline structures of these compounds or their optical isomers, racemates, diastereoisomers or enantiomers.

Preferably, —$NR^1R^2$ is a saturated nitrogen-containing ring of formula:

with $R^a$ and m being as defined above. Preferably, $R^a$ is a hydrogen atom and m is 4 or 5.

More preferably, —$NR^1R^2$ is selected from the group consisting in piperidyl, pyrrolidinyl.

Preferably, the nitrogen-containing ring i) is one of mono- and di-substituted; more preferably mono-substituted with an alkyl group, such as with a methyl group.

According to a preferred aspect, the substituent(s) is(are) in beta-position with respect to the nitrogen atom.

Preferably, $Y^{II}$ represents a phenyl group at least mono-substituted with a halogen atom, keto-substituent which may include a linear or branched chain aliphatic ketone comprising from 1 to 8 carbon atoms and optionally bearing a hydroxyl group, a cycloalkylketone, an arylalkylketone or arylalkenylketone in which the aryl group is optionally substituted, or a heteroaryl ketone.

More preferably, $Y^{II}$ is a phenyl group at least mono-substituted with a halogen atom, —CHO, a ketone, an aldehyde, —CH=CH—CHO, —C(alkyl)=N—OH, —C(alkyl)=N—O(alkyl), —CH=N—OH, —CH=NO(alkyl), —C(cycloalkyl)=NOH, —C(cycloalkyl)=N—O(alkyl).

According to a more preferred aspect, compounds of formula (IIa) are selected from:
3-Phenylpropyl 3-piperidinopropyl ether
3-(4-Chlorophenyl)propyl 3-piperidinopropyl ether
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chlorophenyl)propyl 3-(3,5-cis-dimethyl piperidino)propyl ether
3-(4-Chlorophenyl)propyl 3-(3,5-trans-dimethyl piperidino)propyl ether.

or their pharmaceutically acceptable salts, hydrates, or hydrated salts, or the polymorphic crystalline structures of these compounds or their optical isomers, racemates, diastereoisomers or enantiomers.

According to a still more preferred aspect, a compound of formula (IIa) is selected from 3-(4-chlorophenyl)propyl-3-piperidinopropylether, or its pharmaceutically acceptable salts, hydrates, or hydrated salts, or the polymorphic crystalline structures of this compound or its optical isomers, racemates, diastereoisomers or enantiomers Preferably, compounds are in the form of a pharmaceutically acceptable salt and said salt is chosen from the group consisting in hydrochloride, hydrobromide, hydrogen maleate or hydrogen oxalate. The hydrochloride salt of 3-(4-chlorophenyl)propyl-3-piperidinopropylether is preferred.

According to a third aspect, non-imidazole compounds analogous to the compounds disclosed in EP 197 840 are described herein.

Thus, a sub-class of compounds (A) comprises compounds having the following formula (III)

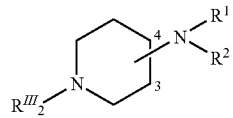

in which:
$NR^1R^2$ is either in 3-position or in 4-position on the piperidyl moiety, $R^1$ and $R^2$ being as defined with reference to formula (A);
$R_2^{III}$ denotes a linear or branched alkyl group having 1 to 6 carbon atoms; a piperonyl group, a 3-(1-benzimidazolonyl)propyl group; a group of formula

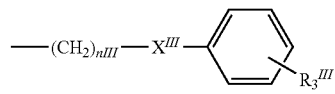

in which $n_{III}$ is 0, 1, 2 or 3, $X^{III}$ is a single bond or alternatively —O—, —S—, —NH—, —CO—, —CH=CH— or

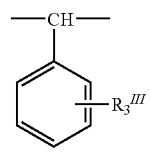

and $R_3^{III}$ is H, $CH_3$, halogen, CN, $CF_3$ or an acyl group —$COR_4^{III}$, $R_4^{III}$ being a linear or branched alkyl group having 1 to 6 carbon atoms, a cycloalkyl group having 3 to 6 carbon atoms or a phenyl group which can bear a $CH_3$ or F substituent; or alternatively a group of formula

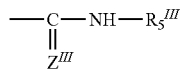

in which $Z^{III}$ denotes an O or S atom or a divalent group NH, N—$CH_3$ or N—CN and $R_5^{III}$ denotes a linear or branched alkyl group having 1 to 8 carbon atoms, a cycloalkyl group having 3 to 6 carbon atoms which can bear a phenyl substituent, a ($C_3$-$C_6$ cycloalkyl) (linear or branched, $C_1$-$C_3$ alkyl) group, a phenyl group which can bear a $CH_3$, halogen or $CF_3$ substituent, a phenyl(linear or branched, $C_1$-$C_3$ alkyl) group or a naphthyl, adamantyl or p-toluenesulphonyl group.

Preferred compounds (III) are those with $R^{III}$ representing the group

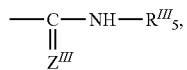

$Z^{III}$ and $R^{III}_5$ being as above-defined and $Z^{III}$ is especially O, S or NH.

Preferred group $R^{III}_5$ is a ($C_3$-$C_6$)cycloalkyl group.

Preferred $R^1$ and $R^2$ groups are as above-described in formula (A).

An example of such compound (III) is N'-Cyclohexylthiocarbamoyl-N-1,4'-bipiperidine (compound 123).

According to a fourth aspect, a sub-class of compounds (A) includes the compounds which have the following formula (IV), analogous to compounds disclosed in EP 494 010:

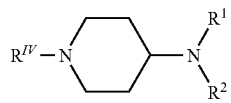

in which
$R^1$ and $R^2$ are as defined with reference to general formula (A);
$R^{IV}$ represents a hydrogen atom or a group $COR_3^{IV}$, in which $R_3^{IV}$ represents
(a) a linear or branched aliphatic group containing 1 to 11, and in particular 1 to 9, carbon atoms;
(b) a cyclane ring-system such as cyclopropane, phenylcyclopropane, cyclobutane, cyclopentane, cyclohexane, cycloheptane, norbornane, adamantane, noradamantane, chlorooxonorbornane, chloroethylenedioxynorbornane, bromoethylenedioxynorbornane and the anhydride group of hydroxycarboxy-1,2,2-trimethylcyclopentanecarboxylic acid;
(c) a benzene ring, unsubstituted or substituted at the para-position with a linear or branched aliphatic group containing 3 to 5 carbon atoms, as well as with a halogen;
(d) a group $(CH_2)_{m_{IV}}R_4^{IV}$ in which $m_{IV}$ is a number between 1 and 10, and $R_4^{IV}$ represents a cyclane ring system such as cyclopropane, cyclobutane, cyclopentane, cyclopentene, cyclohexane, cycloheptane, norbornane, noradamantane, adamantane and 6,6-dimethylbicyclo[3.1.1]heptene; a benzene ring, unsubstituted or monosubstituted with a fluorine atom, a chlorine atom, a methyl group or a methoxy group; a thiophene ring grafted via its ring-position 2 or its ring-position 3; a carboxylic acid ester group $COOR_5^{IV}$, in which $R_5^{IV}$ is a cyclane ring-system such as cyclopropane, cyclobutane, cyclopentane, cyclohexane or norbornane; a carboxylic acid amide group of structure $CONHR_6^{IV}$, in which $R_6^{IV}$ represents a cyclane ring-system such as cyclopropane, cyclobutane, cyclopentane, cyclohexane or norbornane; a carboxylic acid amide group of structure

in which the group

represents pyrrolidine, piperidine or 2,6-dimethylmorpholine; or an ether group —O—$R_7^{IV}$, it being possible for $R_7^{IV}$ to be a benzene ring, unsubstituted or monosubstituted with a chlorine or fluorine atom or disubstituted with a chlorine atom and with a methyl group;
(e) a group —CH=$CHR_8^{IV}$, in which $R_8^{IV}$ represents a cyclane ring-system such as cyclopropane, cyclobutane, cyclopentane, cyclohexane, norbornane or norbornene;
(f) a secondary amine group —NH$(CH_2)_{n_{IV}}R_9^{IV}$, in which $n_{IV}$ is a number between 1 and 5 and $R_9^{IV}$ constitutes a cyclane ring-system such as cyclopropane, cyclobutane, cyclopentane, cyclohexane or norbornane, or a benzene ring, unsubstituted, mono-substituted with a fluorine or chlorine atom or with a methoxy group or trisubstituted with methoxy groups;
$R^{IV}$ also represents a hydroxyalkenyl group

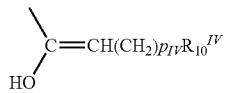

in which $p_{IV}$ is a number between 2 and 9 and $R_{10}^{IV}$, represents a benzene ring or a phenoxy group; as well as a group

in which $n_{IV}$ is a number between 1 and 5 and $R_9^{IV}$ has the meaning stated above.

Preferred compounds (IV) are those in which $R^{IV}$ represents the group $COR_3^{IV}$, $R_3^{IV}$ representing especially an aliphatic group a).

An example of compound (IV) is N-Heptanoyl-1,4'-bipiperidine or 1-(5-Cyclohexylpentanoyl)-1,4-bipiperidine.

According to a fifth aspect, the application describes non-imidazole compounds analogous to those disclosed by Plazzi et al. (Eur. J. Med. Chem. 1995, 30, 881).

Thus, another sub-class of compounds (A) comprises compounds having the following formula (V):

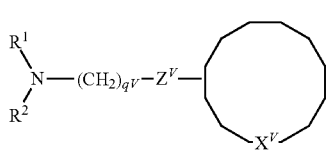

in which
R$^1$ and R$^2$ are as defined with reference to formula (A) in claim 1;
q$^V$ is 2 to 5
Z$^V$ represents NH, O or S
X$_V$ represents a heterocycle, optionally condensed, containing one or more heteroatoms like nitrogen, oxygen or sulfur, unsubstituted or substituted by one or more groups like aryl, lower alkyl and halogen.

Preferred compounds are those with X$^V$ being an heterocycle like:

(Va)

(Vb)

(Vc)

with Y$^V$ representing an hydrogen atom, an halogen or a lower alkyl.

Examples of compounds (V) are:
2-((2-Piperidinoethyl)amino)benzothiazole
2-(6-Piperidinohexylamino)benzothiazole
4-(6-Piperidinohexylamino)quinoline
2-Methyl 4-(3-piperidinopropylamino)quinoline
2-Methyl 4-(6-piperidinohexylamino)quinoline
7-Chloro-4-(3-piperidinopropylamino)quinoline
7-Chloro-4-(4-piperidinobutylamino)quinoline
7-Chloro-4-(8-piperidinooctylamino)quinoline
7-Chloro-4-(10-piperidinodecylamino)quinoline
7-Chloro-4-(12-piperidinododecylamino)quinoline
7-Chloro-4-(4-(3-piperidinopropoxy)phenylamino)quinoline
7-Chloro-4-(2-(4-(3-piperidinopropoxy)phenyl)ethylamino)quinoline According to a sixth aspect, the application describes non-imidazole compounds which are analogous to those disclosed in WO 95/14007.

Thus, another subclass of compounds (A) includes the compounds having the following formula (VI):

(VI)

wherein:
A$^{VI}$ is selected from —O—CO—NR$^1_{VI}$—, —O—CO—, —NR$^1_{VI}$—CO—, —NR$^1_{VI}$—, —NR$^1_{VI}$—, —CO—, —NR$^1_{VI}$—, —O—, —CO—NR$^1_{VI}$—, —CO—O—, and —C(=NR$^1_{VI}$)—NR$^1_{VI}$—;

the groups R$^1_{VI}$, which may be the same or different when there are two or three such groups in the molecule of formula VI, are selected from hydrogen, and lower alkyl, aryl, cycloalkyl, heterocyclic and heterocyclyl-alkyl groups, and groups of the formula —(CH$_2$)$_{yVI}$-G$^{VI}$, where G$^{VI}$ is selected from CO$_2$R$^3_{VI}$, COR$^3_{VI}$, CONR$^3_{VI}$R$^4_{VI}$, OR$^3_{VI}$, SR$^3_{VI}$, NR$^3_{VI}$R$^4_{VI}$, heteroaryl and phenyl, which phenyl is optionally substituted by halogen, lower alkoxy or polyhaloloweralkyl, and y$_{VI}$ is an integer from 1 to 3;

R$^2_{VI}$ is selected from hydrogen and halogen atoms, and alkyl, alkenyl, alkynyl and trifluoromethyl groups, and groups of the formula OR$^3_{VI}$, SR$^3_{VI}$ and NR$^3_{VI}$R$^4_{VI}$;

R$^3_{VI}$ and R$^4_{VI}$ are independently selected from hydrogen, and lower alkyl and cycloalkyl groups, or R$^3_{VI}$ and R$^4_{VI}$ together with the intervening nitrogen atom can form a saturated ring containing 4 to 6 carbon atoms that can be substituted with one or two lower alkyl groups;

the group —(CH$_2$)$_{nVI}$-A$^{VI}$-R$^1_{VI}$ is at the 3- or 4-position, and the group R$^2_{VI}$ is at any free position;

m$_{VI}$ is an integer from 1 to 3;
and n$_{VI}$ is 0 or an integer from 1 to 3.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

lower alkenyl (in R$^2_{VI}$)—represents a straight or branched aliphatic hydrocarbon radical having at least one carbon-to-carbon double bond (preferably in conjugation with the benzene ring that the group R$^2$ substitutes) and having from 2 to 6 carbon atoms;

lower alkynyl (in R$^2_{VI}$)—represents a straight or branched aliphatic hydrocarbon radical having at least one carbon-to-carbon triple bond (preferably in conjugation with the benzene ring that the group R$^2$ substitutes) and having from 2 to 6 carbon atoms;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 Y$_{VI}$ groups, each independently selected from halo, alkyl, hydroxy, loweralkyoxy, phenoxy, amino, loweralkylamino, diloweralkylamino, and polyhaloloweralkyl. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6;

halogen—represents fluorine, chlorine, bromine and iodine;

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms; e.g., 2- or 3-piperidinyl, 2- or 3-piperazinyl, 2- or 3-morpholinyl, or 2- or 3-thiomorpholinyl;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 2-, 4- or 5-pyrimidinyl, 2-pyrazinyl, or 3- or 4-pyridazinyl, etc.

Preferred heteroaryl groups are 2-, 3- and 4-pyridyl;

heterocyclyl-alkyl—represents a heterocyclic group defined above substituting an alkyl group; e.g., 2-(3-piperidinyl)-ethyl, (2-piperazinyl)-methyl, 3-(2-morpholinyl)-propyl, (3-thiomorpholinyl)-methyl, 2-(4-pyridyl)-ethyl, (3-pyridyl)-methyl, or (2-thienyl)-methyl.

Preferably, $A^{VI}$ is $-CH_2-NR^1{}_{VI}-$ or especially $-C(=NH)-NR^1{}_{VI}-$ preferred compounds include those wherein $m_{VI}$ is 1 or 2, and $n_{VI}$ is 0, 1 or 2.

Other preferred values of A include $-O-CO-NR^1{}_{VI}-$, $-O-$, and $-CO-O-$. In all these compounds, the groups $R^1{}_{VI}$ are as defined above, and the side chain is preferably at the 4-position. In compounds of formula VI, one group $R^1{}_{VI}$ is preferably selected from hydrogen, 2-phenylethyl, 4-chlorophenylmethyl, 4-methoxyphenylmethyl, 4-trifluoromethylphenylmethyl and 4-pyridylmethyl, but is especially 4-chlorophenylmethyl; any other group $R^1{}_{VI}$ that is present is preferably a hydrogen atom or a methyl group.

Particularly preferred compounds are those wherein $n_{VI}$ and $m_{VI}$ are each 1, and $A^{VI}$ represents an oxygen atom.

$R^1{}_{VI}$ is preferably an aryl or $-(CH_2)_{y,VI}-G^{VI}$ with $G^{VI}$ being a phenyl.

$R^1$ and $R^2$ are preferably selected as specified with reference to formula (A).

Another sub-class of compounds (A) comprises compounds of formula (VI) wherein $R^1{}_{VI}$ represents an aryl group, especially a phenyl optionally substituted with a keto substituent, $R^2{}_{VI}$, $n_{VI}$, $m_{VI}$ and $A^{VI}$ having the above-meaning.

The keto substituent is as above-defined in $Y^{II}$ with reference to compounds (IIa) and (IIb).

Preferred compounds are those with $n_{VI}$ and $m_{VI}$ being each 1 and $A^{VI}$ being an oxygen atom.

Examples of compounds VI are:

α-(Acetylphenoxy)-α'-piperidino p-xylol

α-(4-Acetylphenoxy)-α'-(1-pyrrolidinyl)p-xylol

α-(3-Phenylpropoxy)-α'-piperidino p-xylol

α-(4-Acetylphenoxy)-α'-(4-methylpiperidino)p-xylol

α-(4-Acetylphenoxy)-α'-(3,5-cis-dimethylpiperidino)p-xylol

α-(4-Acetylphenoxy)-α'-(3,5-trans-dimethylpiperidino)p-xylol

α-(4-Acetylphenoxy)-α'-(2-methylpyrrolidino)p-xylol

α-(4-Cyclopropylcarbonylphenoxy)-α'-piperidino-p-xylol

α-(4-Cyclopropylcarbonylphenoxy)-α'-(4-methylpiperidino)p-xylol

α-(4-Cyclopropylcarbonylphenoxy)-α'-pyrrolidino-p-xylol

N-(4-Chlorobenzyl)-2-(4-piperidino methyl)phenyl)ethanamidine

According to a seventh aspect, it is herein described another sub-class of compounds (A) including non-imidazole compounds having the following formula (VII) which are analogous to compounds disclosed in Clitherow et al. (Bioorg. & Med. Chem. Lett., 6 (7), 833, 1996):

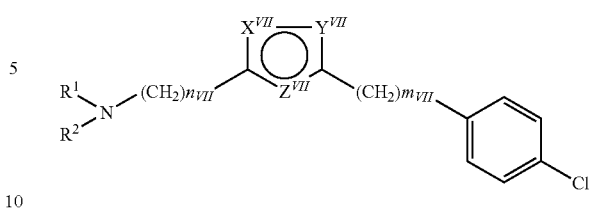

(VII)

in which $R^1$ and $R^2$ are as defined in reference to formula (A);

$X^{VII}$, $Y^{VII}$ and $Z^{VII}$ are identical or different and represent O, N or S;

$n_{VII}$ is varying from 1 to 3;

$m_{VII}$ is 1 or 2.

$n_{VII}$ is preferably 2 or 3, especially 2 and $m_{VII}$ is preferably 1.

Preferred compounds are those with $X^{VII}$ being 0 and $Y^{VII}$ and $Z^{VII}$ each being N to represent a 1, 2, 4-oxadiazolyl group.

An illustrative compound is given in example 130.

According to a eighth aspect, the application describes another sub-class of compounds (A) including the non-imidazole compounds having the following formula (VIII), which are analogous to those disclosed in WO 95/06037:

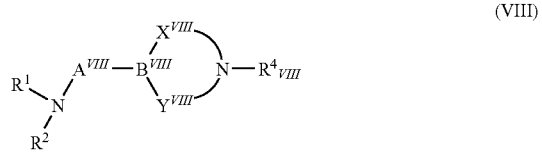

(VIII)

wherein $R^1$ and $R^2$ are as defined with reference to formula (A) and wherein $A^{VIII}$ is 1) a group of the formula $(CH_2)_{m_{VIII}}$, wherein $m_{VIII}=0-9$; or 2) a group of the formula:

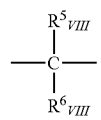

wherein $R^5{}_{VIII}$ represents hydrogen, $(C_1-C_3)$alkyl-, aryl$(C_1-C_3)$alkyl-, aryl-, wherein aryl may optionally be substituted, hydroxyl-, $(C_1-C_3)$alkoxy-, halogen, amino-, cyano- or nitro; and $R^6{}_{VIII}$ represents hydrogen, $(C_1-C_3)$alkyl-, aryl$(C_1-C_3)$alkyl-, or aryl-, wherein aryl may optionally be substituted; or 3) a group of the formula:

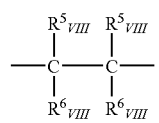

wherein $R^5{}_{VIII}$ and $R^6{}_{VIII}$ are as defined above; or 4) a group of the formula:

if $B^{VIII}$ is a group of the formula:

such that $A^{VIII}$ and $B^{VIII}$ together form a group of the formula:

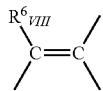

wherein $R^6_{VIII}$ is as defined above; or
 5) a group of the formula:

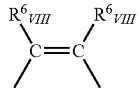

wherein $R^6_{VIII}$ is as defined above; or
 6) a group of the formula:

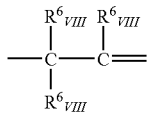

if $B^{VIII}$ is a group of the formula:

such that $A^{VIII}$ and $B^{VIII}$ together form a group of the formula:

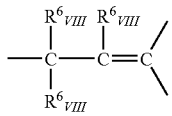

wherein $R^6_{VIII}$ is as defined above; or
 7) a group of the formula:

wherein $x_{VIII}+y_{VIII}=m_{VIII}-1$;

$B^{VIII}$ is
 1) a group of the formula:

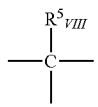

wherein $R^5_{VIII}$ is as defined above; or
 2) a group of the formula:

if A is a group of one of the formulas:

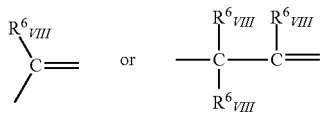

such that A and B together form a group of one of the formulas:

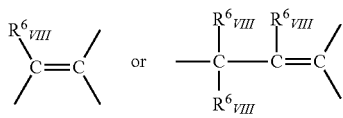

wherein $R^6_{VIII}$ is as defined above; or
 3) a group of the formula:

if $X^{VIII}$ is a group of the formula:

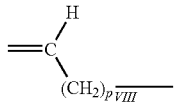

such that $B^{VIII}$ and $X^{VIII}$ together form a group of the formula

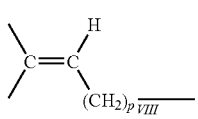

wherein $p_{VIII}=1\text{-}3$; or $X^{VIII}$ is 1) a group of the formula $(CH_2)_{n_{VIII}}$ wherein $n_{VIII}=2\text{-}4$; or
2) a group of the formula:

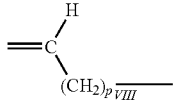

if $B^{VIII}$ is a group of the formula:

such that $X^{VIII}$ and $B^{VIII}$ together form a group of the formula:

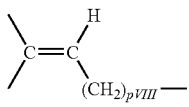

wherein $p_{VIII}=1\text{-}3$; or 3) two hydrogens (one on the carbon and one on the nitrogen); or
4) one hydrogen on the carbon atom and one $R^7_{VIII}$ group on the nitrogen atom, wherein $R^7_{VIII}$ represents hydrogen, $(C_1\text{-}C_{10})$alkyl-, aryl $(C_1\text{-}C_{10})$alkyl-, or aryl, wherein aryl may optionally be substituted;

$Y^{VIII}$ is a group of the formula $(CH_2)_{k_{VIII}}$, wherein $k_{VIII}=0\text{-}2$;

$R^4_{VIII}$ represents hydrogen, $(C_1\text{-}C_{10})$alkyl-, $(C_1\text{-}C_3)$alkyl-sulfonamide-, aryl$(C_1\text{-}C_{10})$alkyl-, aryl, wherein aryl may optionally be substituted;

or a group of the formula:

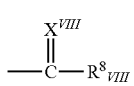

or a group of the formula:

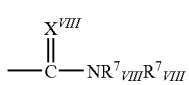

wherein $X^{VIII}$ represents O, S, or NH, $R^7_{VIII}$ is as defined as above;

$R^8_{VIII}$ represents $(C_1\text{-}C_{10})$alkyl-, aryl$(C_1\text{-}C_{10})$alkyl- or aryl, wherein aryl may optionally be substituted and wherein aryl is phenyl, substituted phenyl, naphtyl, substituted naphtyl, pyridyl.

Both linear and ringstructured compounds are encompassed.

The linear compounds have for example one of the formulas $$R^1\text{\textbackslash}N(R^2)\text{—}(CH_2)_n^{VIII}\text{—}NH_2 \quad \text{(VIIIa)}$$

$$R^1\text{\textbackslash}N(R^2)\text{—}(CH_2)_n^{VIII}\text{—}NH\text{—}C(=S)\text{—}NH\text{—}R^{VIII} \quad \text{(VIIIb)}$$

Preferred $R^1$ and $R^2$ groups are as defined with reference to formula (A).

A compound (VIII) is described in examples 132 and 169.

According to a ninth aspect, the instant application describes a sub-class of compounds (A) consisting of compounds having the following formula (IX) which are analogous to those described in WO 97/29092:

$$R^1\text{\textbackslash}N(R^2)\text{—}X^{IX}_{m_{IX}}\text{—}N(R^2_{IX})\text{—}S(=O)_2\text{—}N(R^2_{IX})\text{—}R^1_{IX} \quad \text{(IX)}$$

wherein:

$R^1$ and $R^2$ are as defined with reference to formula (A)

$R^1_{IX}$ is $C_4$ to $C_{20}$ hydrocarbyl (in which one or more hydrogen atoms may be replaced by halogen, and up to four carbon atoms [and especially from 0 to 3 carbon atoms] may be replaced by oxygen, nitrogen or sulphur atoms, provided that $R^1_{IX}$ does not contain an —O—O-group), $R^2_{IX}$ identical or different, are H or $C_1$ to $C_{15}$ hydrocarbyl (in which one or more hydrogen atoms may be replaced by halogen, and up to three carbon atoms may be replaced by oxygen, nitrogen or sulphur atoms, provided that $R^2_{IX}$ does not contain an —O—O-group), $m_{IX}$ is from 1 to 15 (preferably 1 to 10, more preferably 3 to 10, eg. 4 to 9)

each $X^{IX}$ group is independently $$-\underset{R^4_{IX}}{\overset{R^3_{IX}}{C}}-,$$

or one $X^{IX}$ group is —N($R^4_{IX}$)—, —O— or —S— (provided that this $X^{IX}$ group is not adjacent the —N$R^2_{IX}$— group) and the remaining $X^{IX}$ groups are independently $$-\underset{R^4_{IX}}{\overset{R^3_{IX}}{C}}-,$$

wherein $R^3_{IX}$ is H, $C_1$ to $C_6$ alkyl, $C_2$ to $C_6$ alkenyl, —CO$_2$R$^5_{IX}$, —CON(R$^5_{IX}$)$_2$, —CR$^5_{IX2}$OR$^6_{IX}$ or —OR$^5_{IX}$ (in which $R^5_{IX}$ and $R^6_{IX}$ are H or $C_1$ to $C_3$ alkyl), and $R^4_{IX}$ is H or $C_1$ to $C_6$ alkyl.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups.

A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

When reference is made herein to a substituted carbocyclic group (such as substituted phenyl), or a substituted heterocyclic group, the substituents are preferably from 1 to 3 in number and selected from $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulphamoyl and cyano.

The term "halogen", as used herein, refers to any of fluorine, chlorine, bromine and iodine.

Preferably, $R^2_{IX}$ is selected from H, $C_1$ to $C_6$ alkyl, $C_1$ to $C_6$ cycloalkyl, $C_1$ to $C_6$ hydroxyalkyl, $C_1$ to $C_6$ alkylhydroxyalkyl, aryl $C_1$ to $C_6$ alkyl and substituted aryl $C_1$ to $C_6$ alkyl. For example, $R^2_{IX}$ may be H or $C_1$ to $C_3$ alkyl.

In certain embodiments, $—X^{IX}_{mIX}—$ is a $C_1$ to $C_8$ alkylene group, e.g. a butylene group.

Included in the definition of $R^1_{IX}$ are aryl-containing groups (such as phenyl, substituted phenyl, naphthyl and substituted naphthyl), and (cycloalkyl)alkyl groups (such as cyclohexylpropyl and adamantylpropyl).

Preferably, $R^1_{IX}$ is a group of the formula

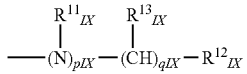

wherein
$p_{IX}$ is 0 or 1,
$R^{11}_{IX}$ is H or $C_1$ to $C_3$ alkyl,
$q_{IX}$ is from 0 to 4,
$R^{12}_{IX}$ is a carboxylic, substituted carbocyclic, heterocyclic or substituted heterocyclic group, and
$R^{13}_{IX}$ is independently selected from H, $C_1$ to $C_6$ alkyl, $C_1$ to $C_6$ cycloalkyl, $C_1$ to $C_6$ hydroxyalkyl, $C_1$ to $C_6$ alkylhydroxyalkyl, aryl $C_1$ to $C_6$ alkyl and substituted aryl $C_1$ to $C_6$ alkyl.

Preferably, $R^{13}_{IX}$ is hydrogen.

Compounds (IX) wherein $R^1_{IX}$ is a group $—NH—CH_2—$Ph where Ph represents an optionally substituted phenyl, are preferred.

Preferred groups $R^1$ and $R^2$ are as specified with reference to formula (A).

An illustrative example is compound 173.

According to a tenth aspect, another sub-class of compounds (A) is described that comprises compounds having the following formula (X), which are analogous to compounds disclosed by Wolin et al. (Bioorg. & Med. Chem. Lett., 8, 2157 (1998)):

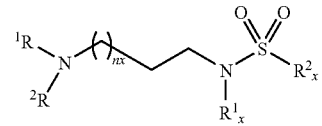

wherein:
$R^1$ and $R^2$ are as defined with reference to formula (A);
$R^1_x$ is H or $CH_3$;
$R^2_x$ is selected from a phenyl optionally substituted with a halogen atom, preferably chlorine, a ($C_1$-$C_4$)alkyl, a ($C_1$-$C_4$)alkoxy, $CF_3$, $OCF_3$, $NO_2$, $NH_2$; or a $CH_2$-phenyl optionally substituted as above-specified;
$n_x$ is from 0 to 3.
$n_x$ is preferably 1. $R^2$ is preferably a phenyl group, especially a mono-substituted phenyl group.
Preferred $R^1$ and $R^2$ are as above-specified for formula (A).
Compound 174 is illustrative of compounds (X).

According to an eleventh aspect, the application describes non-imidazole compounds which are analogous to those disclosed in WO 96/38142.

Thus, another sub-class of compounds (A) is directed to compounds having the following formula (XI):

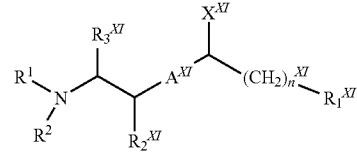

where $R^1$ and $R^2$ are as defined with reference to formula (A);
where $A^{XI}$ is $—NHCO—$, $—N(CH_3)—CO—$, $—NHCH_2—$, $—N(CH_3)—CH_2—$, $—CH=CH—$, $—COCH_2—$, $CH_2CH_2—$, $—CH(OH)CH_2—$, or $—C\equiv C—$;
$X^{XI}$ is H, $CH_3$, $NH_2$, $NH(CH_3)$, $N(CH_3)_2$, OH, $OCH_3$, or SH;
$R_2^{XI}$ is hydrogen or a methyl or ethyl group;
$R_3^{XI}$ is hydrogen or a methyl or ethyl group;
$n^{XI}$ is 0, 1, 2, 3, 4, 5 or 6; and
$R_1^{XI}$ is selected from the group consisting of $C_3$ to $C_8$ cycloalkyl; phenyl or substituted phenyl; decahydronaphthalene and octahydroindene; or
$R_1^{XI}$ and $X^{XI}$ may be taken together to denote a 5,6 or 6,6 saturated bicyclic ring structure when $X^{XI}$ is NH, O, S, or $SO_2$.

Preferably for compounds of formula (XI):
$A^{XI}$ is $—NHCO—$, $—N(CH_3)—CO—$, $—NHCH_2—$, $—N(CH_3)—CH_2—$, $—CH=CH—$, $—COCH_2—$, $—CH_2CH_2—$, $—CH(OH)CH_2—$, or $—C\equiv C—$;
$X^{XI}$ is H, $CH_3$, $NH_2$, $NH(CH_3)$, $N(CH_3)_2$, OH, $OCH_3$, or SH;
$R_2^{XI}$ is hydrogen or a methyl or ethyl group;
$R_3^{XI}$ is hydrogen or a methyl or ethyl group;
$n^{XI}$ is 0, 1, 2, 3, 4, 5, or 6; and
$R_1^{XI}$ is selected from the group consisting of (a) $C_3$ to $C_8$ cycloalkyl; (b) phenyl or substituted phenyl; (d) heterocyclic (e) decahydronaphthalene and (f) octahydroindene; or
$R_1^{XI}$ and $X^{XI}$ may be taken together to denote a 5,6 or 6,6 saturated bicyclic ring structure when $X^{XI}$ can be NH, O, or S.

More preferably, the present invention provides compounds
where $A^{XI}$ is $—NHCH_2—$, $—N(CH_3)—CH_2—$, $—CH=CH—$, —COCH$_2$—, —CH$_2$CH$_2$, —CH(OH)CH$_2$—, or —C≡C—;

X$^{XI}$ is H, CH$_3$, NH$_2$, NH(CH$_3$), N(CH$_3$)$_2$, OH, OCH$_3$, or SH;

R$_2^{XI}$ is hydrogen or a methyl or ethyl group;
R$_3^{XI}$ is hydrogen or a methyl or ethyl group;
n$^{XI}$ is 0, 1, 2, 3, 4, 5, or 6; and
R$_1^{XI}$ is selected from the group consisting of (a) C$_3$ to C$_8$ cycloalkyl; (b) phenyl or substituted phenyl; (d) heterocyclic; (e) decahydronaphthalene and (f) octahydroindene; or R$_1^{XI}$ and X$^{XI}$ may be taken together to denote a 5,6 or 6,6 saturated bicyclic ring structure when X$^{XI}$ can be NH, O, or S.

Most preferably, the present invention provides compounds
where A$^{XI}$ is —CH=CH or —C≡C—;
X$^{XI}$ is H, CH$_3$ or NH$_2$;
R$_2^{XI}$ and R$_3^{XI}$ are H;
n$^{XI}$ is 1, 2, or 3;
R$_1^{XI}$ is selected from the group consisting of (a) C$_3$ to C$_8$ cycloalkyl; (b) phenyl or substituted phenyl; (d) heterocyclic; (e) decahydronaphthalene and (f) octahydroindene; or R$_1^{XI}$ and X$^{XI}$ may be taken together to denote a 5,6 or 6,6 saturated bicyclic ring structure when X$^{XI}$ is NH, O, or S.

The term "substituted phenyl" as used herein refers to a phenyl group substituted by one or more groups such as alkyl, halogen, amino, methoxy and cyano groups.

The term "alkyl" refers to straight or branched chain radicals.

Representative examples of alkyl groups include methyl, ethyl, n-propyl, isopropyl, n-butyl, sec-butyl, iso-butyl, tert-butyl and the like.

Compounds (XI) where A$^{XI}$ is —CH=CH— or —C≡C—, X$^{XI}$, R$_2^{XI}$ and R$_3^{XI}$ are each H, n$_{XI}$ is 1 and R$_1^{XI}$ is a C$_3$-C$_8$ cycloalkyl, are especially preferred.

R$^1$ and R$^2$ are preferably selected as above-indicated in reference to formula (A).

Representative particularly preferred compounds are compounds 177, 178 or 179.

According to a twelfth aspect, it is herein described non-imidazole compounds which are analogous to those disclosed in WO 96/38141.

These compounds have the following formula (XII):

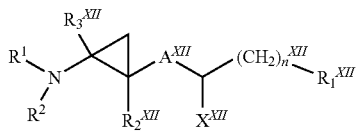

where R$^1$ and R$^2$ are as defined in reference to formula (A),
where R$_2^{XII}$ is a hydrogen or a methyl or ethyl group;
R$_3^{XII}$ is a hydrogen or a methyl or ethyl group;
n$^{XII}$ is 0, 1, 2, 3, 4, 5, or 6; and
R$_1^{XII}$ is selected from the group consisting of (a) C$_3$ to C$_8$ cycloalkyl; (b) phenyl substituted or not by one or more groups such as a halogen atom, a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, x-hydroxyalkyl, alkenyl, alkynyl, sulphamido, sulfamoyl, sulphonamido, carboxamide, carbonylcycloalkyl, alkylcarbonylalkyl, carboalkoxy, arylalkyl or oxime group, or two substituents taken together with the carbon atoms of the phenyl ring to which it is fused form 5- or 6-membered saturated or unsaturated ring or a benzene ring; (c) alkyl; (d) heterocyclic; (e) decahydronaphthalene; and (f) octahydroindene;

with the provisos that
when X$^{XII}$ is H, A$^{XII}$ can be —CH$_2$CH$_2$—, —COCH$_2$—, —CONH—, —CON(CH$_3$)—, —CH=CH—, —C≡C—, —CH$_2$—NH—, —CH$_2$—N(CH$_3$)—, —CH(OH)CH$_2$—, —NH—CH$_2$—, —N(CH$_3$)—CH$_2$—, —CH$_2$O—, —CH$_2$S—, or —NHCOO—;

when X$^{XII}$ is NH$_2$, NH(CH$_3$), N(CH$_3$)$_2$, OH, OCH$_3$, CH$_3$, SH or SCH$_3$; A$^{XII}$ can be —NHCO—, —N(CH$_3$)—CO—, —NHCH$_2$—, —N(CH$_3$)—CH$_2$—, —CH=CH—, —COCH$_2$—, —CH$_2$CH$_2$—, —CH(OH)CH$_2$—, or —C≡C—; and when R$_1^{XII}$ and X$^{XII}$ taken together denote a 5,6 or 6,6 saturated bicyclic ring structure X$^{XII}$ can be NH, O, or S.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "substituted phenyl" as used herein refers to a phenyl group substituted by one or more groups such as alkyl, halogen, amino, methoxy, and cyano groups.

The term "bicyclic alkyl" as used herein refers to an organic compound having two ring structures connected to an alkyl group. They may or may not be the same type of ring and the rings may be substituted by one or more groups. Representative bicyclic alkyl groups include adamanthyl, decahydronaphthalene and norbornane.

The cyclopropane attached to the NR$^1$R$^2$ moiety is preferably in trans configuration.

More preferably, it is described compounds of the general formula (XII):
where A$^{XII}$ is —CONH, —CH=CH—, —NHCOO—, or —C≡C—;
X$^{XII}$ is H or NH$_2$;
R$_2^{XII}$ and R$_3^{XII}$ are H;
n$^{XII}$ is 0, 1, 2 or 3;
R$_1^{XII}$ is cyclohexyl, phenyl or substituted phenyl.

In compounds (XII), A$^{XII}$ is especially —CH=CH— or —C≡C—;
R$_2^{XII}$, R$_3^{XII}$ and X$^{XII}$ are each especially a hydrogen atom;
n$_{XII}$ is preferably 1 and R$_1^{XII}$ is especially an alkyl group.

R$^1$ and R$^2$ are preferably selected as above-indicated with reference to formula (A).

Representative example of compounds (XII) is compound 180.

According to a thirteenth aspect, to the instant application describes non-imidazole compounds analogous to those disclosed in WO 95/11894.

Thus, the sub-class of compounds (A) comprises compounds having the following formula (XIII):

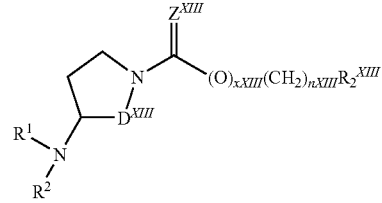

wherein $R^1$ and $R^2$ are as defined with reference to formula (A)

wherein $D^{XIII}$ is $CH_2$ or $CH_2$—$CH_2$, $Z^{XIII}$ represents sulfur (S) or oxygen (O), preferably O, $X_{XIII}$ is 0 or 1, $n_{XIII}$ is an integer from 0 to 6, and $R_2^{XIII}$ represents a substituted or unsubstituted linear chain or branched chain alkyl group of up to about 20 carbon atoms, a substituted or unsubstituted carbocyclic group of up to about 20 carbon atoms including mono and bicyclic moieties, and a substituted or an unsubstituted aryl group of up to about 20 carbon atoms, or any combination of above-mentioned groups, or salts thereof and with the substituants being represented by one or more groups such as a halogen atom, a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, α-hydroxyalkyl, alkenyl, alkynyl, sulphamido, sulfamoyl, sulphonamido, carboxamide, carbonylcycloalkyl, alkylcarbonylalkyl, carboalkoxy, arylalkyl or oxime group, or two substituents taken together with the carbon atoms of the phenyl ring to which it is fused form 5- or 6-membered saturated or unsaturated ring or a benzene ring.

In a specific embodiment, $R_2^{XIII}$ can represents a disubstituted methyl, such as but not limited to dicyclohexyl methyl (—$CH(C_6H_{11})_2$), diphenyl methyl (—$CH(C_6H_5)_2$), and the like. If $R_2^{XIII}$ is tert-butyl, cyclohexyl, or dicyclohexylmethyl, $X_{XIII}$ or $n_{XIII}$ must not be 0. If $R_2^{XIII}$ is adamantane, the sum of $x_{XIII}$ and $n_{XIII}$ must be greater than 1.

In a preferred embodiment, $D^{XIII}$ is $CH_2$—$CH_2$, resulting in a piperidine ring structure. However, it is contemplated that $D^{XIII}$ can be $CH_2$, yielding a pyrrolidine ring structure. In yet another embodiment, $D^{XIII}$ can be $(CH_2)_3$, yielding a cycloheptimide (seven membered heterocycle with one nitrogen).

In a specific embodiment, a tetramethylene bound to the amide or carbamate group is used. Preferably a cyclic alkyl or aryl group is linked to the amide or carbamate via the straight chain alkyl group. In a specific embodiment, tetramethylene cyclohexane (cyclohexylbutyl) is bound to an amide. Although specific hydrophobic alkyl and aryl groups have been mentioned, one of ordinary skill in the art will recognize that there are many possible hydrophobic groups for use in the compounds of the invention. These fall within the scope of the instant invention.

Thus, $R_2^{XIII}$ can be one or more bulky substituent groups. As stated above, in a preferred aspect of the invention, the bulky substituents are removed from the amide or carbamate group on the piperidyl, by increasing $n_{XIII}$. In one embodiment, $R_2^{XIII}$ is $CHR_3^{XIII}R_4^{XIII}$, in which $n_{XIII}$ is 3 or 4 and $R_3^{XIII}$ and $R_4^{XIII}$ are cyclohexyl, phenyl, or the like. $R_3^{XIII}$ and $R_4^{XIII}$ can be the same group or different groups. In another embodiment, $R_2^{XIII}$ is decalin or adamantane or the like. If $R_2^{XIII}$ is adamantane, preferably $n_{XIII}$ is greater than 1, but the sum of $x_{XIII}$ and $n_{XIII}$ must be greater than 1.

As used herein, the phrase linear chain or branched chained alkyl groups of up to about 20 carbon atoms means any substituted or unsubstituted acyclic carbon-containing compounds, including alkanes, alkenes and alkynes. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; and lower alkylene, for example, ethylene, propylene, propyldiene, butyldiene, butyldiene, and the like. The ordinary skilled artisan is familiar with numerous linear and branched alkyl groups, which are with the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. Such cyclic groups may also contain various substituents in which one or more hydrogen atoms has been replaced by a functional group. Such functional groups include those described above, and lower alkyl groups as describe above. The cyclic groups of the invention may further comprise a heteroatom. For example, in a specific embodiment, $R_2^{XIII}$ is cyclohexanol.

As used herein, substituted and unsubstituted aryl groups means a hydrocarbon ring bearing a system of conjugated double bonds, usually comprising six or more even number of π (pi) electrons, Examples of aryl groups include, by are not limited to, phenyl, naphthyl, anisyl, toluoyl, xylenyl and the like. According to the present invention, aryl also includes heteroaryl groups, e.g., pyrimidine or thiophene. These aryl groups may also be substituted with any number of a variety of functional groups. In addition to the functional groups described above in connection with substituted alkyl groups and carbocyclic groups, functional groups on the aryl groups can be nitro groups.

As mentioned above, $R_2^{XIII}$ can also represents any combination of alkyl, carbocyclic or aryl groups, for example, 1-cyclohexylpropyl, benzyl cyclohexylmethyl, 2-cyclohexylpropyl, 2,2-methylcyclohexylpropyl, 2,2-methylphenylpropyl, 2,2-methylphenylbutyl.

In a specific embodiment, $R_2$ represents cyclohexane, and $n_{XIII}$=4 (cyclohexylvaleroyl). In another specific embodiment, $R_2^{XIII}$ represents cinnamoyl.

Particularly preferred are compounds (XIII) wherein $Z^{XIII}$ is an oxygen atom and wherein $x_{XIII}$ is 0 or 1, $n_{XIII}$ is an integer from 0 to 6, more preferably $n_{XIII}$=3-6, and most preferably $n_{XIII}$=4, and $R_2^{XIII}$ is as defined above. Examples of preferred alkyl groups for $R_2^{XIII}$ include but are not limited to cyclopentyl, cyclohexyl, admantane methylene, dicyclohexyl methyl, decanyl and t-butyryl and the like. Examples of preferred aryl and substituted aryl groups include but are not limited to phenyl, aryl cyclohexyl methyl and the like.

Preferred $R^1$ and $R^2$ are selected as indicated with reference to formula (A).

Representative examples are compounds 123 and 176.

According to a fourteenth aspect, the application describes compounds analogous to those disclosed in WO 93/12107.

Thus, a sub-class of compounds (A) concerns compounds having the following formula (XIV)

(XIV)

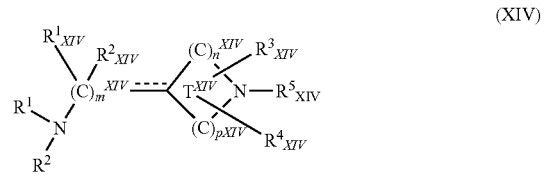

wherein $R^1$ and $R^2$ are as defined in reference of formula (A); (A) $m_{XIV}$ is an integer selected from the group consisting of: 1 and 2;

(B) $n_{XIV}$ and $p_{XIV}$ are integers and are each independently selected from the group consisting of: 0, 1, 2, 3, and 4 such that the sum of $n_{XIV}$ and $p_{XIV}$ is 4 and $T^{XIV}$ is a 6-membered ring;

(C) $R^3{}_{XIV}$ and $R^4{}_{XIV}$ are each independently bound to the same or different carbon atom of ring $T^{XIV}$ such that there is only one $R^3{}_{XIV}$ group and one $R^4{}_{XIV}$ group in ring $T^{XIV}$, and each $R^1{}_{XIV}$, $R^2{}_{XIV}$, $R^3{}_{XIV}$ and $R^4{}_{XIV}$ is independently selected from the group consisting of:
  (1) H;
  (2) $C_1$ to $C_6$ alkyl; and
  (3) —$(CH_2)_{qXIV}$—$R^6{}_{XIV}$ wherein $q_{XIV}$ is an integer of: 1 to 7, and $R^6{}_{XIV}$ is selected from the group consisting of: phenyl, substituted phenyl, —$OR^7{}_{XIV}$, —$C(O)OR^7{}_{XIV}$, —$C(O)R^7{}_{XIV}$, —$OC(O)R^7{}_{XIV}$, —$C(O)NR^7{}_{XIV}R^8{}_{XIV}$, CN and —$SR^7{}_{XIV}$ wherein $R^7{}_{XIV}$ and $R^3{}_{XIV}$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents;

(D) $R^5{}_{XIV}$ is selected from the group consisting of:
  (1) H;
  (2) $C_1$ to $C_{20}$ alkyl;
  (3) $C_3$ to $C_6$ cycloalkyl;
  (4) —$C(O)OR^{7'}{}_{XIV}$ wherein $R^{7'}{}_{XIV}$ is the same as $R^7{}_{XIV}$ defined below except that $R^{7'}{}_{XIV}$ is not H;
  (5) —$C(O)R^{7'}{}_{XIV}$;
  (6) —$C(O)NR^7{}_{XIV}R^8{}_{XIV}$;
  (7) allyl;
  (8) propargyl; and
  (9) —$(CH_2)_q$—$R^6{}_{XIV}$ wherein $q_{XIV}$ and $R^6{}_{XIV}$ are as defined above, and when $q_{XIV}$ is equal to 1, then $R^6{}_{XIV}$ is not OH or SH;

(E) $R^7{}_{XIV}$ and $R^8{}_{XIV}$ are each independently selected from the group consisting of: H, $C_1$ to $C_6$ alkyl, and $C_3$ to $C_6$ cycloalkyl;

(F) the dotted line (-------) represents a double bond that is optionally present when $m_{XIV}$ is 1, and $n_{XIV}$ is not 0, and p is not 0 (i.e., the nitrogen in the ring is not bound directly to the carbon atom bearing the double bond), and when said double bond is present then $R^2{}_{XIV}$ is absent; and (G) when $m_{XIV}$ is 2, each $R^1{}_{XIV}$ is the same or different substituent for each $m_{XIV}$, and each $R^2{}_{XIV}$ is the same or different substituent for each $m_{XIV}$, and at least two of the substituents $R^1{}_{XIV}$ and/or $R^2{}_{XIV}$ are H.

Those skilled in the art will appreciate that the total number of substituents on each of the —$(C)_n{}^{XIV}$— and —$(C)_p{}^{XIV}$— groups is two, and that such substituents are independently selected from the group consisting of hydrogen, $R^3{}_{XIV}$ and $R^4{}_{XIV}$ such that there is a total of only one $R^3{}_{XIV}$ and one $R^4{}_{XIV}$ substituent in ring $T^{XIV}$.

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms;

halogen (halo)—represents fluoro, chloro, bromo or iodo.

Preferably, for compounds of formula (XIV) m is 1; $R^5{}_{XIV}$ is selected from the group consisting of H and $C_1$ to $C_{15}$ alkyl; and $R^1{}_{XIV}$ to $R^4{}_{XIV}$ are each independently selected from the group consisting of: H, $C_1$ to $C_6$ alkyl, and —$(CH_2)_{qXIV}$—$R^6{}_{XIV}$ wherein $R^6{}_{XIV}$ is phenyl, Most preferably, $R^5{}_{XIV}$ is selected from the group consisting of H and $C_1$ to $C_6$ alkyl with H and methyl being even more preferable; and $R^3{}_{XIV}$ and $R^4{}_{XIV}$ are each independently selected from the group consisting of: H and methyl, Representative compounds include compounds of the formula:

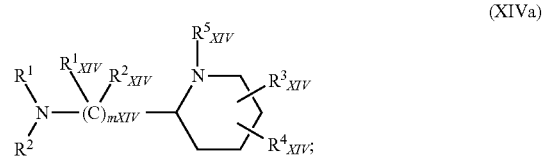

(XIVa)

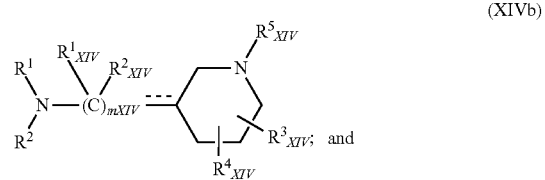

(XIVb)

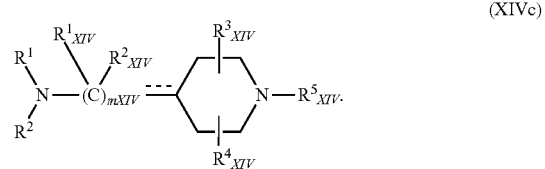

(XIVc)

For formula (XIVa), (XIVb) or (XIVc), $R^5{}_{XIV}$ is preferably H or $CH_3$; $R^3{}_{XIV}$ and $R^4{}_{XIV}$ are preferably each an hydrogen atom.

Preferred $R^1$ and $R^2$ are as specified for formula (A).

According to a fifteenth aspect, the application describes to 2 compounds analogous to those disclosed in WO 93/12108. Thus, these compounds have the following formula (XV):

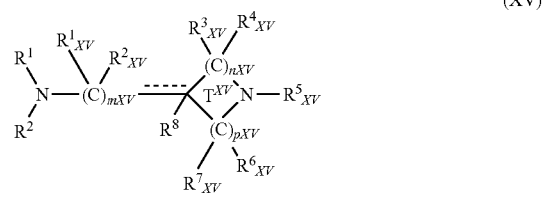

(XV)

wherein $R^1$ and $R^2$ are as defined in reference to formula (A)

(A) $m_{XV}$ is an integer selected from the group consisting of: 0, 1, and 2;

(B) $n_{XV}$ and $p_{XV}$ are integers and are each independently selected from the group consisting of: 0, 1, 2, and 3 such that the sum of $n_{XV}$ and $p_{XV}$ is 2 or 3 such that when the sum of $n_{XV}$ and $p_{XV}$ is 2, $T^{XV}$ is a 4-membered ring and when the sum of $n_{XV}$ and $p_{XV}$ is 3, $T^{XV}$ is a 5-membered ring;

(C) each $R^1{}_{XV}$, $R^2{}_{XV}$, $R^3{}_{XV}$, $R^4{}_{XV}$, $R^6{}_{XV}$, $R^7{}_{XV}$ and $R^8{}_{XV}$ is independently selected from the group consisting of:
  (1) H;
  (2) $C_1$ to $C_6$ alkyl;
  (3) $C_3$ to $C_6$ cycloalkyl; and
  (4) —$(CH_2)_q{}^{XV}$—$R^9{}_{XV}$ wherein $q_{XV}$ is an integer of: 1 to 7, and $R^9{}_{XV}$ is selected from the group consisting of: phenyl, substituted phenyl, —$OR^{10}{}_{XV}$, —$C(O)OR^{10}{}_{XV}$, —$C(O)R^{10}{}_{XV}$, —$OC(O)R^{10}{}_{XV}$, —$C(O)NR^{10}{}_{XV}R^{11}{}_{XV}$, CN and —$SR^{10}{}_{XV}$ wherein $R^{10}{}_{XV}$ and $R^{11}{}_{XV}$ are as defined below, and wherein the substituents on said substituted phenyl are each independently selected from the group consisting of: —OH, —O—($C_1$ to $C_6$) alkyl, halogen, $C_1$ to $C_6$ alkyl, —$CF_3$, —CN, and —$NO_2$, and wherein said substituted phenyl contains from 1 to 3 substituents; examples of —$(CH_2)_{qXV}$—$R^9_{XV}$ include benzyl, substituted benzyl and the like, wherein the substitutents on the substituted benzyl are as defined above for said substituted phenyl;

(D) $R^5_{XV}$ is selected from the group consisting of:

(1) H;

(2) $C_1$ to $C_{20}$ alkyl;

(3) $C_3$ to $C_6$ cycloalkyl;

(4) —$C(O)OR^{10'}_{XV}$; wherein $R^{10'}_{XV}$ is the same as $R^{10}_{XV}$ defined below except that $R^{10'}_{XV}$ is not H;

(5) —$C(O)R^{10}_{XV}$;

(6) —$C(O)NR^{10}_{XV}R^{11}_{XV}$;

(7) allyl;

(8) propargyl; and (9) —$(CH_2)_q^{XV}$—$R^9_{XV}$, wherein $q_{XV}$ and $R^9_{XV}$ are as defined above with the proviso that when $q_{XV}$ is 1 then $R^9_{XV}$ is not —OH or —SH;

(E) $R^{10}_{XV}$ and $R^{11}_{XV}$ are each independently selected from the group consisting of: H, $C_1$ to $C_6$ alkyl, and $C_3$ to $C_6$ cycloalkyl; and, for the substituent —$C(O)NR^{10}_{XV}R_{XV}^{11}$, $R^{10}_{XV}$ and $R^{11}_{XV}$, together with the nitrogen to which they are bound, can form a ring having 5, 6, or 7 atoms;

(F) the dotted line (--------) represents a double bond that is optionally present when $m_{XV}$ is 1, and $T^{XV}$ is a 5-membered ring, and $n_{XV}$ is not 0, and $p_{XV}$ is not 0 (i.e., the nitrogen in the ring is not bound directly to the carbon atom bearing the double bond), and when said double bond is present then $R^2_{XV}$ and $R^8_{XV}$ are absent;

(G) when $m_{XV}$ is 2, each $R^1_{XV}$ is the same or different substituent for each $m_{XV}$, and each $R^2_{XV}$ is the same or different substituent for each $m_{XV}$;

(H) when $n_{XV}$ is 2 or 3, each $R^3_{XV}$ is the same or different substituent for each $n_{XV}$, and each $R^4_{XV}$ is the same or different substituent for each $n_{XV}$; and (I) when $p_{XV}$ is 2 or 3, each $R^6_{XV}$ is the same or different substituent for each p, and each $R^7_{XV}$ is the same or different substituent for each $p_{XV}$.

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms; and halogen (halo)—represents fluoro, chloro, bromo or iodo.

Preferably, for compounds of formula (XV) $m_{XV}$ is 0 or 1; $R^5_{XV}$ is selected from the group consisting of H and $C_1$ to $C_{20}$ alkyl; and $R^1_{XV}$ to $R^4_{XV}$ and $R^6_{XV}$ to $R^8_{XV}$ are each independently selected from the group consisting of: H, $C_1$ to $C_6$ alkyl, and —$(CH_2)_{qXV}$—$R^9_{XV}$ wherein $R^9_{XV}$ is phenyl. Most preferably, $R^5_{XV}$ is selected from the group consisting of H and methyl; and $R^1_{XV}$, $R^2_{XV}$, $R^3_{XV}$, $R^4_{XV}$, $R^6_{XV}$, $R^7_{XV}$, and $R^8_{XV}$ are each independently selected from the group consisting of: H, methyl, ethyl, pentyl, benzyl, and 2-phenylethyl, Representative compounds include compounds of the formula:

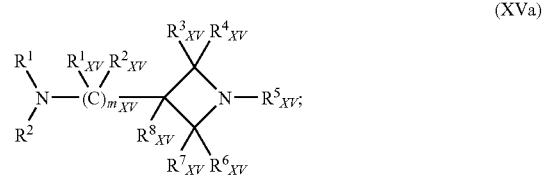
(XVa)

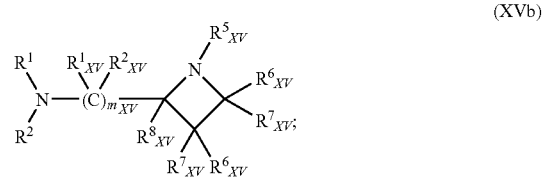
(XVb)

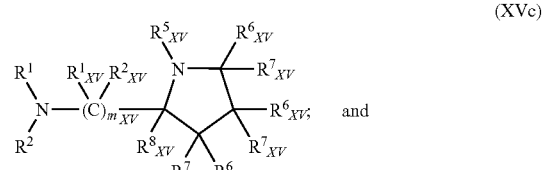
(XVc)

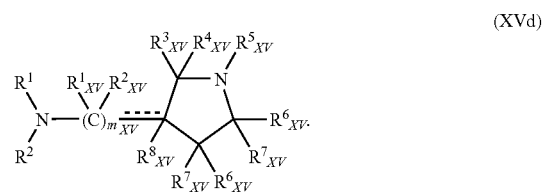
(XVd)

wherein $m_{XV}$ and $R^1_{XV}$ to $R^8_{XV}$ are as defined for formula (XV)

Compounds (XVc) or (XVd) are preferred.

Representative compounds (XVa) to (XVd) are those wherein $R^5_{XV}$ is H or $CH_3$.

Preferably, only one or two of substituents $R^3_{XV}$, $R^4_{XV}$, $R^6_{XV}$, $R^7_{XV}$, $R^8_{XV}$ is different from H and represents especially $CH_3$.

$R^1$ and $R^2$ are preferably selected as indicated in reference to formula (A).

According to a sixteenth aspect, the application describes to compounds analogous to those disclosed in WO 92/15567.

Thus, this sub-class of compounds (A) consists of compounds having the following formula (XVI)

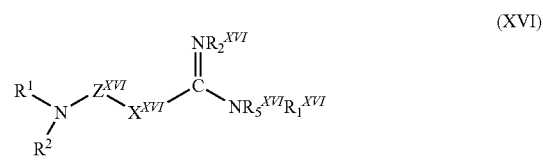
(XVI)

wherein $R^1$ and $R^2$ are as defined in reference to formula (A)

$Z^{XVI}$ is a group of the formula $(CH_2)_{mXVI}$ wherein $m_{XVI}$=1-5 or a group of the formula:

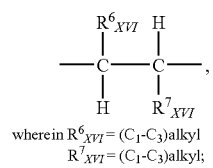

wherein $R^6_{XVI}$ = (C$_1$-C$_3$)alkyl
$R^7_{XVI}$ = (C$_1$-C$_3$)alkyl;

wherein $Z^{XVI}$ may optionally comprise other substituents selected such that the activity of the derivative is not negatively affected, $X^{XVI}$ represents S, NH or CH$_2$ $R^1_{XVI}$ represents hydrogen, (C$_1$-C$_3$)alkyl-, aryl(C$_1$-C$_{10}$)alkyl, wherein aryl may optionally be substituted, aryl, (C$_5$-C$_7$)cycloalkyl(C$_1$-C$_{10}$)alkyl-, or a group of the formula:

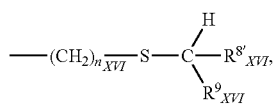

wherein $n_{XVI}$=1-4, $R^8_{XVI}$ is aryl, aryl(C$_1$-C$_{10}$)alkyl-, (C$_5$-C$_7$)cycloalkyl- or (C$_5$-C$_7$)cycloalkyl(C$_1$-C$_{10}$)alkyl-, and $R^9_{XVI}$ is hydrogen, (C$_1$-C$_{10}$)alkyl- or aryl; $R_2^{XVI}$ and $R_5^{XVI}$ represent hydrogen, (C$_1$-C$_3$)alkyl-, aryl or arylalkyl-, wherein aryl may optionally be substituted; wherein aryl is phenyl, substituted phenyl, naphthyl, substituted naphthyl, pyridyl or substituted pyridyl;

$R_2^{XVI}$ and $R_5^{XVI}$ are preferably a hydrogen atom.

$m_{XVI}$ is preferably 2 or 3

$X^{XVI}$ is preferably S or NH $R_1^{XVI}$ is preferably selected from H or an optionally substituted aryl.

Preferred $R^1$ and $R^2$ are selected as specified for formula A.

According to a seventeenth aspect, a sub-class of compounds (A) comprises compounds having the following formula (XVII), which can be considered as analogous to those disclosed in EP 680 960:

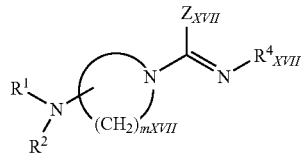

(XVII)

wherein $m_{XVII}$ represents an integer of from 4 to 6.

$R^4_{XVII}$ represents a hydrogen atom, a linear or branched alkyl group, a cycloalkyl group, a cycloalkylalkyl group, a substituted or unsubstituted aryl group or a substituted or unsubstituted aralkyl group; and $Z^{XVII}$ represents $R^5_{XVII}$ or $A^{XVII}$-$R^6_{XVII}$, wherein $A^{XVII}$ represents S or O, $R_5^{XVII}$ represents a hydrogen atom, a lower alkyl group, a substituted or unsubstituted aryl group or a substituted or unsubstituted aralkyl group, and $R_6^{XVII}$ represents a lower alkyl group, a lower alkenyl group, a lower alkynyl group or a substituted or unsubstituted aralkyl group;

The lower alkyl groups are preferably linear or branched alkyl groups having 1 to 6 carbon atoms. Specific examples thereof include methyl, ethyl, n-propyl, iso-propyl, n-butyl, iso-butyl, sec-butyl, tert-butyl, n-pentyl and n-hexyl groups.

The linear or branched alkyl groups are preferably those having 1 to 8 carbon atoms. Specific examples thereof include methyl, ethyl, n-propyl, iso-propyl, n-butyl, iso-butyl, sec-butyl, tert-butyl, n-pentyl, n-hexyl, 1,1-dimethylpropyl, 1,2-dimethylpropyl and 1,2,2-trimethylpropyl groups.

The cycloalkyl groups are preferably those having 3 to 10 carbon atoms. The cycloalkyl groups include not only monocycloalkyl groups (for example, cyclopentyl, cyclohexyl and cycloheptyl) but also polycycloalkyl groups (for example, bicycloalkyl and tricycloalkyl). Examples of the bicycloalkyl groups include norbornyl (for example, exo-2-norbornyl and endo-2-norbornyl), 3-pinanyl and bicyclo[2.2.2]oct-2-yl groups, while examples of the tricycloalkyl groups include adamantyl groups (for example, 1-adamantyl and 2-adamantyl). Such a cycloalkyl group may be substituted by alkyl group(s), etc.

The cycloalkylalkyl groups are preferably those composed of a cycloalkyl group having 3 to 10 carbon atoms with a linear or branched alkyl group having 1 to 3 carbon atoms. Specific examples thereof include 1-cyclohexylethyl and 1-cyclopropylethyl groups.

The lower alkenyl groups are preferably linear or branched alkenyl groups having 3 to 6 carbon atoms. Specific examples thereof include allyl, 1-methyl-2-propenyl, 2-methyl-2-propenyl, cis-2-butenyl, trans-2-butenyl and 3-methyl-2-butenyl groups.

The lower alkynyl groups are preferably those having 3 to 6 carbon atoms. A specific example thereof includes a 2-propynyl group.

The substituted aryl groups are preferably phenyl and naphthyl groups which may be substituted by halogen atoms and trifluoromethyl, lower alkyl, lower alkoxy, lower alkylthio, cyano and nitro groups.

Specific examples thereof include phenyl, 1-naphthyl, 2-chlorophenyl, 3-chlorophenyl, 4-chlorophenyl, 4-trifluoromethylphenyl, 3-fluorophenyl, 4-fluorophenyl, 2-methoxyphenyl, 4-methoxyphenyl, 2-tolyl and 3-tolyl groups.

The aralkyl groups are preferably benzyl, diarylmethyl and trityl groups.

The substituted aralkyl groups are preferably arylalkyl groups composed of a phenyl or naphthyl group, which may be substituted by halogen atoms and trifluoromethyl, lower alkyl, lower alkoxy, lower alkylthio, cyano and nitro groups, and a linear or branched alkyl group having 1 to 4 carbon atoms.

Specific examples thereof include benzyl, α-methylbenzyl, phenethyl, 3-phenylpropyl, 4-phenylbutyl, 4-chlorobenzyl, 4-fluorobenzyl, 4-methoxybenzyl, 4-chloro-α-methylbenzyl, 4-fluoro-αmethylbenzyl and 4-methoxy-α-methylbenzyl groups.

Among the compounds represented by the general formula (XVII) preferable examples include those wherein:

$m_{XVII}$ is from 4 to 6;

$R^4_{XVII}$ is a hydrogen atom; a linear or branched alkyl group having 1 to 8 carbon atoms, a cycloalkyl group having 3 to 10 carbon atoms, a cycloalkylalkyl group composed of a cycloalkyl moiety having 3 to 10 carbon atoms and an alkyl moiety having 1 to 3 carbon atoms, a substituted or unsubstituted aryl group or a substituted or unsubstituted aralkyl group carrying an alkyl moiety having 1 to 4 carbon atoms;

$R^5_{XVII}$ is a hydrogen atom, an alkyl group having 1 to 6 carbon atoms, a substituted or unsubstituted aryl group or a substituted or unsubstituted aralkyl group carrying an alkyl moiety having 1 to 4 carbon atoms; and $R^6_{XVII}$ is an alkyl group having 1 to 6 carbon atoms, an alkenyl group having 3 to 6 carbon atoms, an alkynyl group having 3 to 6 carbon atoms or a substituted or unsubstituted aryl group.

Preferable examples of the compounds represented by the general formula (XVII) are those satisfying the following requirements:
(1) A compound wherein $m^{XVII}$ is 5 and $R^1$, $R^2$ and $R^3$ are each a hydrogen atom.
(2) A compound wherein $R^4_{XVII}$ is a cycloalkyl group, such as monocycloalkyl, bicycloalkyl and tricycloalkyl groups. A preferable example of the monocycloalkyl group is a cyclohexyl group. A preferable example of the bicycloalkyl group is a norbornyl group, more preferably a 2-exo-norbornyl group. A preferable example of the tricycloalkyl group is an adamantyl group, more preferably a 1-adamantyl group.
(3) A compound wherein $R^4_{XVII}$ is a substituted or unsubstituted phenyl group or a substituted or unsubstituted phenylalkyl group.
(4) A compound wherein $R^5_{XVII}$ is a hydrogen atom,
(5) A compound wherein $A^{XVII}$ is S and $R^6_{XVII}$ is a lower alkyl group.
(6) A compound wherein a lower alkyl group is a methyl group.

$R^1$ and $R^2$ are preferably selected as specified for the formula (A).

According to a eighteenth aspect, the invention is directed to non imidazole compounds having the following formula (XVIII), analogous to those disclosed in Van der Goot et al. (Eur. J. Med. Chem. (1992) 27, 511-517):

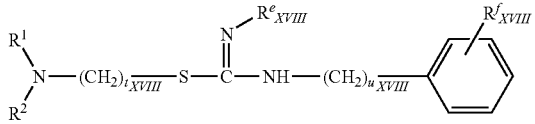

(XVIII)

in which:
$R^1$ and $R^2$ are as defined with reference to formula (A);
$R^e_{XVIII}$ is H, alkyl or cycloalkyl;
$R^f_{XVIII}$ is H or halogen, in particular Cl, F, Br, or an alkyl;
$t_{XVIII}$ is 1 to 3;
$u_{XVIII}$ is 1 to 4.

Preferred groups $R^1$ and $R^2$ are as defined with reference to formula (A).

Representative example is compound 122 and 167.

The W residue as defined in formula (A) and in particular as illustrated by formulae (I) to (XVIII), preferably contains no imidazole moiety attached in 4(5)-position and more preferably W contains no imidazole moiety.

The compounds may be prepared according to one of the schemes described in the international patent application WO 00/06254.

Treatment of Parkinson's Disease, Obstructive Sleep Apnea, Dementia with Lewy Bodies and/or Vascular Dementia and Their Symptoms The compounds of formula (A) according to the invention have antagonistic and/or agonistic properties at the histamine $H_3$-receptors. They affect the synthesis and release of histamine monoamines or neuropeptides in brain and peripheral tissues.

The inventors have now demonstrated that the $H_3$-receptor antagonists/inverse agonists as described herein are able to treat the wakefulness/sleep disorders of PD, OSA, narcolepsy, DLB, VD.

The invention thus provides a method of treatment of Parkinson's disease, obstructive sleep apnea, narcolepsy, dementia with Lewy bodies and/or vascular dementia, comprising administering a patient in need thereof with a therapeutically effective amount of a compound of formula (A), as described above, optionally in combination with a therapeutically acceptable vehicle or excipient.

The invention also relates to the use of a compound of formula (A) for the manufacture of a medicament intended for the treatment of Parkinson's disease, obstructive sleep apnea, narcolepsy, dementia with Lewy bodies and/or vascular dementia.

The invention also refers to a combination with a compound of formula (A) as defined above with an anti-parkinson drug.

As used herein, the treatment of Parkinson's disease, obstructive sleep apnea, narcolepsy, dementia with Lewy bodies and/or vascular dementia encompasses the treatment of associated disorders, especially the treatment of sleep and vigilance disorders associated therewith.

Preferably, a compound of formula (A) intended for the treatment of Parkinson's disease, obstructive sleep apnea, narcolepsy, dementia with Hi Lewy bodies and/or vascular dementia is a compound of formula (I) to (XVIII).

Still preferably, a method of treatment of Parkinson's disease, obstructive sleep apnea, narcolepsy, dementia with Lewy bodies and/or vascular dementia comprises administering a patient in need thereof with a therapeutically effective amount of at least one following compounds:
1-(5-phenoxypentyl)-piperidine
1-(5-phenoxypentyl)-pyrrolidine
N-methyl-N-(5-phenoxypentyl)-ethylamine
1-(5-phenoxypentyl)-morpholine
N-(5-phenoxypentyl)-hexamethyleneimine
N-ethyl-N-(5-phenoxypentyl)-propylamine
1-(5-phenoxypentyl)-2-methyl-piperidine
1-(5-phenoxypentyl)-4-propyl-piperidine
1-(5-phenoxypentyl)-4-methyl-piperidine
1-(5-phenoxypentyl)-3-methyl-piperidine
1-acetyl-4-(5-phenoxypentyl)-piperazine
1-(5-phenoxypentyl)-3,5-trans-dimethyl-piperidine
1-(5-phenoxypentyl)-3,5-cis-dimethyl-piperidine
1-(5-phenoxypentyl)-2,6-cis-dimethyl-piperidine
4-carboethoxy-1-(5-phenoxypentyl)-piperidine
3-carboethoxy-1-(5-phenoxypentyl)-piperidine
1-[3-(4-cyclopropylcarbonylphenoxy)propyl]-piperidine
1-[3-(4-acetylphenoxy)-2-R-methylpropyl]piperidine
1-[3-(4-cyanophenoxy)propyl]-4-methylpiperidine
1-[3-(4-cyanophenoxy)propyl]-3-methylpiperidine
1-[3-(4-acetylphenoxy)-2-S-methylpropyl]piperidine
1-{3-[4-(3-oxobutyl)phenoxy]propyl}piperidine
1-[3-(4-cyano-3-fluorophenoxy)propyl]piperidine
1-[3-(4-nitrophenoxy)propyl]-3-methylpiperidine
1-[3-(4-cyanophenoxy)propyl]-2-methylpiperidine
1-[3-(4-nitrophenoxy)propyl]-2-methylpiperidine
1-[3-(4-nitrophenoxy)propyl]-4-methylpiperidine
1-[3-(4-cyanophenoxy)propyl]-2,6-dimethylpiperidine
1-[3-(4-propionylphenoxy)propyl]-3-methylpiperidine
1-[3-(4-cyclobutylcarbonylphenoxy)propyl]piperidine
1-[3-(4-cyclopentylcarbonylphenoxy)propyl]piperidine
1-[3-(4-cyanophenoxy)propyl]-cis-2-methyl-5-ethylpiperidine
1-[3-(4-cyanophenoxy)propyl]-trans-2-methyl-5-ethylpiperidine
1-[3-(4-cyanophenoxy)propyl]-cis-3,5-dimethylpiperidine
1-[3-(4-propionylphenoxy)propyl]-4-methylpiperidine
1-[3-(4-propionylphenoxy)propyl]-2-methylpiperidine
1-{3-[4-(1-hydroxypropyl)phenoxy]propyl}-3-methylpiperidine 1-{3-[4-(1-hydroxypropyl)phenoxy]propyl}-4-methylpiperidine
1-[3-(4-propionylphenoxy)propyl]-2-methylpiperidine
1-[3-(4-propionylphenoxy)propyl]-4-methylpiperidine methoxime
1-[3-(4-cyanophenoxy)propyl]-trans-3,5-dimethylpiperidine
1-[3-(4-cyclopropylcarbonylphenoxy)propyl]-trans-3,5-dimethyl piperidine
1-[3-(4-cyclopropylcarbonylphenoxy)propyl]-cis-3,5-dimethyl piperidine
1-[3-(4-carbomethoxyphenoxy)propyl]piperidine
1-[3-(4-propenylphenoxy)propyl]-2-methyl piperidine
1-[3-(4-propionylphenoxy)propyl]-2-methylpiperidine
1-{3-[4-(1-ethoxypropyl)phenoxy]propyl}-2-methyl piperidine
1-[3-(4-propionylphenoxy)propyl]-4-methylpiperidine
1-[3-(4-bromophenoxy)propyl]piperidine
1-[3-(4-nitrophenoxy)propyl]piperidine
1-[3-(4-N,N-dimethylsulfonamidophenoxy)propyl]piperidine
1-[3-(4-isopropylphenoxy)propyl]piperidine
1-[3-(4-sec-butylphenoxy)propyl]piperidine
1-[3-(4-propylphenoxy)propyl]piperidine
1-[3-(4-ethylphenoxy)propyl]piperidine
1-(5-phenoxypentyl)-1,2,3,6-tetrahydropyridine
1-[5-(4-nitrophenoxy)-pentyl]-pyrrolidine
1-[5-(4-chlorophenoxy)-pentyl]-pyrrolidine
1-[5-(4-methoxyphenoxy)-pentyl]-pyrrolidine
1-[5-(4-methylphenoxy)-pentyl]-pyrrolidine
1-[5-(4-cyanophenoxy)-pentyl]-pyrrolidine
1-[5-(2-naphthyloxy)-pentyl]-pyrrolidine
1-[5-(1-naphthyloxy)-pentyl]-pyrrolidine
1-[5-(3-chlorophenoxy)-pentyl]-pyrrolidine
1-[5-(4-phenylphenoxy)-pentyl]-pyrrolidine
1-{5-[2-(5,6,7,8-tetrahydronaphthyl)-oxy]-pentyl}-pyrrolidine
1-[5-(3-phenylphenoxy)-pentyl]-pyrrolidine
1-(5-phenoxypentyl)-2,5-dihydropyrrole
1-{5-[1-(5,6,7,8-tetrahydronaphthyl)-oxy]-pentyl}-pyrrolidine
1-(4-phenoxybutyl)-pyrrolidine
1-(6-phenoxyhexyl)-pyrrolidine
1-(5-phenylthiopentyl)-pyrrolidine
1-(4-phenylthiobutyl)-pyrrolidine
1-(3-phenoxypropyl)-pyrrolidine
1-[5-(3-nitrophenoxy)-pentyl]-pyrrolidine
1-[5-(4-fluorophenoxy)-pentyl]-pyrrolidine
1-[5-(4-nitrophenoxy)-pentyl]-3-methyl-piperidine
1-[5-(4-acetylphenoxy)-pentyl]-pyrrolidine
1-[5-(4-aminophenoxy)-pentyl]-pyrrolidine
1-[5-(3-cyanophenoxy)-pentyl]-pyrrolidine
N-[3-(4-nitrophenoxy)-propyl]-diethylamine
N-[3-(4-cyanophenoxy)-propyl]-diethylamine
1-[5-(4-benzoylphenoxy)-pentyl]-pyrrolidine
1-{5-[4-(phenylacetyl)-phenoxy]-pentyl}-pyrrolidine
N-[3-(4-acetylphenoxy)-propyl]-diethylamine
1-[5-(4-acetamidophenoxy)-pentyl]-pyrrolidine
1-[5-(4-phenoxyphenoxy)-pentyl]-pyrrolidine
1-[5-(4-N-benzamidophenoxy)-pentyl]-pyrrolidine
1-{5-[4-(1-hydroxyethyl)-phenoxy]-pentyl}-pyrrolidine
1-[5-(4-cyanophenoxy)-pentyl]-diethylamine
1-[5-(4-cyanophenoxy)-pentyl]-piperidine
N-[5-(4-cyanophenoxy)-pentyl]-dimethylamine
N-[2-(4-cyanophenoxy)-ethyl]-diethylamine
N-[3-(4-cyanophenoxy)-propyl]-dimethylamine
N-[4-(4-cyanophenoxy)-butyl]-diethylamine
N-[5-(4-cyanophenoxy)-pentyl]-dipropylamine
1-[3-(4-cyanophenoxy)-propyl]-pyrrolidine
1-[3-(4-cyanophenoxy)-propyl]-piperidine
N-[3-(4-cyanophenoxy)-propyl]-hexamethyleneimine
N-[6-(4-cyanophenoxy)-hexyl]-diethylamine
N-[3-(4-cyanophenoxy)-hexyl]-dipropylamine
N-3-[4-(1-hydroxyethyl)-phenoxy]-propyl-diethylamine
4-(3-diethylaminopropoxy)-acetophenone-oxime
1-[3-(4-acetylphenoxy)-propyl]-piperidine
1-[3-(4-acetylphenoxy)-propyl]-3-methyl-piperidine
1-[3-(4-acetylphenoxy)-propyl]-3,5-trans-dimethyl-piperidine
1-[3-(4-acetylphenoxy)-propyl]-4-methyl-piperidine
1-[3-(4-propionylphenoxy)-propyl]-piperidine
1-[3-(4-acetylphenoxy)-propyl]-3,5-cis-dimethyl-piperidine
1-[3-(4-formylphenoxy)-propyl]-piperidine
1-[3-(4-isobutyrylphenoxy)-propyl]-piperidine
N-[3-(4-propionylphenoxy)-propyl]-diethylamine
1-[3-(4-butyrylphenoxy)-propyl]-piperidine
1-[3-(4-acetylphenoxy)-propyl]-1,2,3,6-tetrahydropyridine
α-(4-Acetylphenoxy)-α'-(4-methylpiperidino)p-xylol
α-(4-Acetylphenoxy)-α'-(3,5-cis-dimethylpiperidino)p-xylol
α-(4-Acetylphenoxy)-α'-(3,5-trans-dimethylpiperidino)p-xylol
α-(4-Acetylphenoxy)-α'-(2-methylpyrrolidino)p-xylol
α-(4-Cyclopropylcarbonylphenoxy)-α'-piperidino-p-xylol
α-(4-Cyclopropylcarbonylphenoxy)-α'-(4-methylpiperidino)p-xylol
α-(4-Cyclopropylcarbonylphenoxy)-α'-pyrrolidino-p-xylol
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chlorophenyl)propyl 3-(3,5-cis-dimethylpiperidino) propyl ether
3-(4-Chlorophenyl)propyl3-(3,5-trans-dimethylpiperidino) propyl ether
4-(6-Piperidinohexylamino)quinoline
2-Methyl 4-(3-piperidinopropylamino)quinoline
2-Methyl 4-(6-piperidinohexylamino)quinoline
7-Chloro-4-(3-piperidinopropylamino)quinoline
7-Chloro-4-(4-piperidinobutylamino)quinoline
7-Chloro-4-(8-piperidinooctylamino)quinoline
7-Chloro-4-(10-piperidinodecylamino)quinoline
7-Chloro-4-(12-piperidinododecylamino)quinoline
7-Chloro-4-(4-(3-piperidinopropoxy)phenylamino)quinoline
7-Chloro-4-(2-(4-(3-piperidinopropoxy)phenyl)ethylamino)quinoline
4-(6-Piperidinohexanoyl)phenyl 3-piperidinopropyl ether
5-Nitro-2-(5-piperidinopentylamino)pyridine
3-Nitro-2-(6-piperidinopentylamino)pyridine
5-Amino-2-(6-piperidinopentylamino)pyridine
2-(6-Piperidinohexylamino)quinoline
N-(4-Chlorobenzyl)-N'-cyclohexyl-3-piperidinopropyl isothiourea
2-(6-Piperidinohexylamino)benzothiazole
10-Piperidinodecylamine
3-Phenylpropyl 3-(N,N-diethylamino)propyl ether
N-(3-(N,N-Diethylamino)propyl)N'-phenylurea
N-Cyclohexylmethyl-N'-(3-piperidinopropyl)guanidine
N-(4-Bromobenzyl)-N'-(4-piperidinobutyl)sulphamide 3-Chloro-N-(4-piperidinobutyl)-N-methyl-benzene sulphonamide
N-(4-Chlorobenzyl)-2-(4-piperidinomethyl)phenyl)ethan amidine
1-(5-Cyclohexylpentanoyl)-1,4-bipiperidine
cis-1-(6-Cyclohexyl-3-hexen-1-yl)piperidine
trans-1-(6-Cyclohexyl-3-hexen-1-yl)piperidine
1-(2-(5,5-Dimethyl-1-hexin-1-yl)cyclopropyl)piperidine.

According to a preferred embodiment, the method of treatment according to the invention comprises administering a patient in need thereof with a therapeutically effective amount of 3-(4-Chlorophenyl)propyl 3-piperidinopropyl ether, optionally in combination with a therapeutically acceptable vehicle or excipient.

The invention further relates to the use of 3-(4-Chlorophenyl)propyl 3-piperidinopropyl ether for the manufacture of a medicament intended for the treatment of Parkinson's disease, obstructive sleep apnea, narcolepsy, dementia with Lewy bodies and/or vascular dementia, and in particular the treatment of the symptoms thereof.

As used herein, "obstructive sleep apnea" (also referred to herein as "OSA") denotes a breathing disorder that occurs primarily during sleep with consequences that may persist throughout the waking hours in the form of sleepiness. This increasingly well-recognized disease is characterized by periodic collapse of the upper airway during sleep with apneas (periodic cessation of breathing), hypopneas (repetitive reduction in breathing) or a continuous or sustained reduction in ventilation and excessive daytime sleepiness, neurocognitive defects and depression. It affects almost every system in the body, resulting namely in increased incidence of cardiovascular disorders (Qureshi and Ballard, J. Allergy and Clin. Immunol., 2003, 112, 643). There is no known pharmacological treatment for OSA.

"Parkinson's disease" ("PD") refers to idiopathic PD or idiopathic parkinsonism described by James Parkinson in 1817. The clinical tetrad of PD includes tremor at repose, bradykinesia (slowness of voluntary movement) or akinesia (reduced or absent movement), cogwheel or leadpipe rigidity, and postural impairment causing difficulty in turning and a stooped posture. The pathologic hallmark is the presence of intracytoplasmic eosinophillic inclusions (Lewy bodies) in addition to loss of neurons in the substantia nigra pars compacta. In addition to the major signs of PD in the movement initiation and control which constitute the core of the disease a large proportion of PD patients display sleep and vigilance disorders. These "sleep and vigilance disorders associated with PD" include in particular insomnia, disorders of sleep initiation and maintenance, sleep fragmentation, parasomnias, sleep disordered breathing, excessive daytime sleepiness (including "sleep attacks") and circadian dysrhythmia (inversion of sleep-wake rhythm).

Dementia with Lewy bodies results from the accumulation of such bodies in the cortex (whereas their accumulation in the nigro-striatal complex is observed in PD, a related degenerative disease). It is characterized by cognitive impairment, attentional disturbances, hallucinations, depression and sleep disorders.

"Vascular dementia, the second most frequent cause of dementia after Alzheimer's disease, is characterized by acute loss of memory, orientation and executive functions and is often associated with demonstrable cerebrovascular lesions in patients suffering from hypertension, diabetes, hyperlipidemia, sleep apnea for several years"

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

"Anti-parkinson drug" refers to any agent usually used and administered to treat, prevent or minimize the effects of Parkinson's disease.

Common anti-parkinson drugs include levodopa, ropinorole, lisuride, bromocriptine, pramixepole.

The "combinations" of the invention refer to combination of two active ingredients which are administered simultaneously, separately or sequentially.

The compound or medicament according to the invention can be administered via oral, parenteral or topical routes, the active ingredient being combined with a therapeutically suitable excipient or vehicle.

According to the invention, oral administration of the compound or medicament in an appropriate formulation is advantageously used. Formulations which are suitable to be administered orally to a patient include discrete units such as capsules, cachets or tablets each containing a predetermined amount of the compound of formula (A); they also include a powder or granules; as solution or a suspension in an aqueous liquid or a non-aqueous liquid; or as an oil-in-water liquid emulsion or a water-in-oil liquid emulsion.

Actual dosage levels of compounds of formula (A) of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors, e.g. the condition of the patient.

Total daily dose of the compounds useful according to this invention administered to a host in single or divided doses may be in amounts, for example, of from about 0.001 to about 100 mg/kg body weight daily and preferably 0.01 to 10 mg/kg/day. A suitable effective dose will be in general in the range of from 10 to 500 mg per day and of from 1 to 10 mg/day for particularly active compounds.

An example of doses regimen may be a single administration of a H3 antagonists/inverse agonists as described herein (such as 3-(4-Chlorophenyl)propyl 3-piperidinopropyl ether) once a day each morning at an oral dose of 30-50 mg to accompany the usual treatment with dopaminergic agents.

Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

These doses are given on the basis of the compound and should be adapted for the salts, hydrates or hydrated salts thereof.

The amount of each component administered is determined by the attending clinicians taking into consideration the etiology and severity of the disease, the patient condition and age, the potency of each component and other factors.

The invention is now illustrated by the following examples.

EXAMPLE 1

Treatment of the Wakefulness/Sleep Disorders of PD with Histamine H3 Antagonists/Inverse Agonists Parkinsonism was experimentally induced in a group of cats by treatment with the chemical neurotoxin MPTP (1-methyl-4-phenyl-1,2,3,6-tetrahydropyridine) which selectively ablates the dopaminergic neurons and reproduces the motor impairments of human PD. The group of cats displayed a marked disorganization of their sleep-wakefulness patterns.

As assessed by electromyographic and EEG recordings, treatment with BF 2.-649 (3-(4-Chlorophenyl)propyl 3-piperidinopropyl ether), a potent and selective H3-antagonist, at an oral dose of 10 mg/kg, normalized these sleep-wakefulness patterns. Particularly, the long periods of sleep which replace, in this animal model of PD, the succession of periods of sleep and wakefulness, a change likely to correspond to the excessive daytime sleepiness experienced by a large proportion of human patients, were largely suppressed upon administration of this drug.

These data, obtained in a very reliable model of PD, show that treatment with histamine H3 antagonists/inverse agonists is able not only to treat the excessive daytime sleepiness which is so detrimental in the every day life of PD patients, but also to reestablish a normal sleep architecture.

EXAMPLE 2

Treatment of Obstructive Sleep Apnea with Histamine H3 Antagonists/Inverse Agonists In a group of 10 male patients with a diagnostic of OSA, confirmed by polysomnography performed during a night in an hospital setting, an Epswoth score above 12 and a body mass index of less than 35, the effect of a 3-day treatment with BF 2.649 (3-(4-Chlorophenyl)propyl 3-piperidinopropyl ether) was assessed in a single-blind trial against placebo, at a fixed oral dose of 40 mg once a day.

This treatment resulted in all subjects in a clear decrease (by more than 60%) in the number of diurnal somnolence episodes and a total prevention of the occurrence of diurnal sleep episodes. In addition the nocturnal sleep duration was not decreased and its quality was improved. This clinical trial establishes for the first time the utility of H3 antagonists/inverse agonists in OSA.

EXAMPLE 3

Treatment of Dementia with Lewi Bodies with Histamine H3 Antagonists/Inverse Agonists Generally, dementia with Lewi bodies is treated with acetylcholinesterase inhibitors such as donepezil, rivastigmine or gallanthamine. These agents increase the acetylcholine concentration in the is brain extracellular space. Combinations of a compound of the invention and one of these agents were tested on rats. The drug was selected from donepezil, rivastigmine or gallanthamine and administered in combination with 3-(4-Chlorophenyl)propyl 3-piperidinopropyl ether in rats. Analysis of the rat brains by microdialysis showed that the increase of the acetylcholine concentration was potentialised with co-administration of the compound of the invention. The combinations were well tolerated by the rats, in particular in respect of the cardiovascular parameters.

EXAMPLE 4

Treatment of PD with Histamine H3 Antagonists/Inverse Agonists in Combination with an Anti-parkinson Drug Combinations of a compound of the invention and a anti-parkinson drug were tested on rats and humans suffering from Parkinson. The anti-parkinson drug was selected from ropinirole, lisuride, bromocriptine, levodopa, pramiprexole and administered in combination with 3-(4-Chlorophenyl)propyl 3-piperidinopropyl ether at a dose of 40 mg p.o. Motor symptoms were significantly improved. The combination of the invention allowed lower doses of the anti-parkinson drug to be administered.

EXAMPLE 5

Treatment of Narcolepsy with Histamine H3 Antagonists/Inverse Agonists

Two clinical studies were conducted on patients suffering from obstructive sleep apnea (OSA), in a single-blinded or double-blinded trial against placebo with a polysomnographical test on patients.

In both studies, patients were administered with 3-(4-Chlorophenyl)propyl 3-piperidinopropyl ether at 40 mg p.o. once a day during 3 and 7 days.

In both studies, daytime sleepiness was improved in accordance with the Epworth test or according to the frequency of naps or daytime sleepiness occurrences. The average daytime sleepiness could be reduced by up to 50%.

We claim:

1. A method for treating excessive daytime sleepiness comprising administering to a patient in need thereof a compound of formula (IIa):

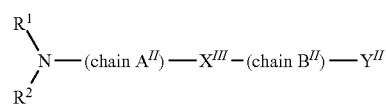

(IIa)

wherein:
R$^1$ and R$^2$ form together with the nitrogen atom to which they are attached a saturated nitrogen-containing ring

i)

with m ranging from 2 to 8, or $R^{a-b}$ being independently a hydrogen atom or a linear or branched alkyl group containing 1 to 6 carbon atoms, and the chain $A^{II}$ selected from an unbranched alkyl group —$(CH_2)_{nII}$— where $n_{II}$ is 3 ;

the group X" is —O—;

the chain $B^{II}$ is an unbranched alkyl comprising 3 carbon atoms; and the group $Y^{II}$ represents a phenyl group, unsubstituted or mono- or polysubstituted with one or more identical or different substituents selected from halogen atoms, $OCF_3$, CHO, $CF_3$, $SO_2N(alkyl)_2$, $NO_2$, S(aryl), $SCH_2$(phenyl), an unbranched or branched alkene, an unbranched or branched alkyne optionally substituted with a trialkylsilyl radical, —O (alkyl), —O(aryl), —$CH_2CN$, a ketone, an aldehyde, a sulphone, an acetal, an alcohol, a linear or branched alkyl group containing 1 to 6 carbon atoms, —CH=CH—CHO, —C(alkyl)=N—OH, —C(alkyl)=N—O(alkyl), —CH=NOH, —CH=NO(alkyl), —C(alkyl)=NH—NH—$CONH_2$, an O-phenyl or —$OCH_2$(phenyl) group, —C(cycloalkyl)=NOH, —C(cycloalkyl)=N—O(alkyl);

or its pharmaceutically acceptable salts, hydrates, or hydrated salts, or the polymorphic crystalline structures of these compounds or their optical isomers, racemates, diastereoisomers or enantiomers, wherein said patient is suffering from Parkinson's disease, narcolepsy, or sleep apnea.

2. The method according to claim 1 wherein —$NR^1R^2$ is a saturated nitrogen-containing ring:

i)

$R^a$ and m being as defined in claim 1.

3. The method according to claim 1, wherein m is 4 or 5.

4. The method according to claim 1, wherein —$NR^1R^2$ is selected from the group consisting in piperidyl, pyrrolidinyl.

5. The method according to claim 1, wherein $R^a$ is a hydrogen atom.

6. The method according to claim 1, wherein the nitrogen-containing ring i) is one of mono- and di-substituted.

7. The method according to claim 1, wherein the nitrogen-containing ring i) is mono-substituted with an alkyl group.

8. The method according to claim 1, wherein the nitrogen-containing ring is mono-substituted with a methyl group.

9. The method according to claim 1, wherein the substituent(s) is(are) in beta-position with respect to the nitrogen atom.

10. The method according to claim 1, wherein $Y^{II}$ represents a phenyl group at least mono-substituted with a halogen atom, keto-substituent which may include a linear or branched chain aliphatic ketone comprising from 1 to 8 carbon atoms and optionally bearing a hydroxyl group, a cycloalkylketone, an arylalkylketone or arylalkenylketone in which the aryl group is optionally substituted, or a heteroaryl ketone.

11. The method according to claim 1, wherein $Y^{II}$ is a phenyl group at least mono-substituted with a halogen atom, —CHO, a ketone, an aldehyde, —CH=CH—CHO, —C(alkyl)=N—OH, —C(alkyl)=N—O(alkyl), —CH=NO(alkyl), -(cycloalkyl)=NOH, —C(cycloalkyl)=N—O (alkyl).

12. The method according to claim 1, wherein the compound is selected from:

- -3-Phenylpropyl 3-piperidinopropyl ether
- -3-(4-Chlorophenyl)propyl 3-piperidinopropyl ether
- -3-Phenylpropyl 3-(4-methylpiperidino)propyl ether
- -3-Phenylpropyl 3-(3,5-cis-dimethylpiperidino)propyl ether
- -3-Phenylpropyl 3-(3,5-trans-dimethylpiperidino)propyl ether
- -3-Phenylpropyl 3-(3-methylpiperidino)propyl ether
- -3-Phenylpropyl 3-pyrrolidinopropyl ether
- -3-(4-Chlorophenyl)propyl 3-(4-methylpiperidino)propyl ether
- -3-(4-Chlorophenyl) propyl 3-(3,5-cis-dimethyl piperidino)propyl ether
- -3-(4-Chlorophenyl) propyl 3-(3,5-trans-dimethyl piperidino)propyl ether, or its pharmaceutically acceptable salts, hydrates, or hydrated salts, or the polymorphic crystalline structures of these compounds or their optical isomers, racemates, diastereoisomers or enantiomers.

13. The method according to claim 1, wherein the compound is selected from 3-(4-chlorophenyl)propyl-3-piperidino- propylether, or its pharmaceutically acceptable salts, hydrates, or hydrated salts, or the polymorphic crystalline structures of this compound or its optical isomers, racemates, diastereoisomers or enantiomers.

14. The method according to claim 1, wherein the compound is in the form of a pharmaceutically acceptable salt and said salt is chosen from the group consisting in hydrochloride, hydrobromide, hydrogen maleate or hydrogen oxalate.

15. A method according to claim 1 further comprising administering a ligand of the H3 receptor in combination with a medicament for treating of Parkinson's disease, obstructive sleep apnea, narcolepsy, dementia with Lewy bodies and/or vascular dementia, respectively.

16. The method according to claim 1 in which said treatment is intended for treating symptoms of Parkinson's disease, obstructive sleep apnea, dementia with Lewy bodies and/or vascular dementia.

17. The method according to claim 16, in which said symptoms are chosen from sleep and vigilance disorders.

18. The method according to claim 15 wherein the antiparkinson drug is chosen from levodopa, ropinorole, lisuride, bromocriptine, pramixepole.

\* \* \* \* \*

UNITED STATES PATENT AND TRADEMARK OFFICE
CERTIFICATE OF CORRECTION

PATENT NO. : 8,486,947 B2
APPLICATION NO. : 11/909778
DATED : July 16, 2013
INVENTOR(S) : Schwartz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1096 days.

Signed and Sealed this
Twenty-third Day of May, 2017

Michelle K. Lee
*Director of the United States Patent and Trademark Office*

UNITED STATES PATENT AND TRADEMARK OFFICE
CERTIFICATE OF CORRECTION

PATENT NO.        : 8,486,947 B2
APPLICATION NO.   : 11/909778
DATED             : July 16, 2013
INVENTOR(S)       : Schwartz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1276 days.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 8,486,947 B2
APPLICATION NO. : 11/909778
DATED : July 16, 2013
INVENTOR(S) : Jean-Charles Schwartz et al.

It is certified that error appears in the above-identified patent and that said Letters Patent is hereby corrected as shown below:

In the Claims

Claim 13, Column 46, Lines 35-36, reads "3-(4-chlorophenyl)propyl-3-piperidino- propylether", which should read "3-(4-chlorophenyl)propyl 3-piperidinopropyl ether".

Signed and Sealed this
Seventeenth Day of October, 2023

Katherine Kelly Vidal
*Director of the United States Patent and Trademark Office*